US012653499B2

(12) United States Patent
Alpert et al.

(10) Patent No.: US 12,653,499 B2
(45) Date of Patent: Jun. 16, 2026

(54) PHYSIOLOGY SENSING INTRALUMINAL DEVICE WITH INDEX FOR SPECTRAL FLOW ASSESSMENT, AND ASSOCIATED DEVICES, SYSTEMS, AND METHODS

(71) Applicant: PHILIPS IMAGE GUIDED THERAPY CORPORATION, San Diego, CA (US)

(72) Inventors: Howard David Alpert, El Dorado Hills, CA (US); Brian Brand Antonius Johannes Bloemendal, Helenaveen (NL); Maarten Petrus Joseph Kuenen, Veldhoven (NL); Arjen Van Der Horst, Tilburg (NL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 18/951,431

(22) Filed: Nov. 18, 2024

(65) Prior Publication Data

US 2025/0072865 A1      Mar. 6, 2025

Related U.S. Application Data

(63) Continuation of application No. 18/094,371, filed on Jan. 8, 2023, now Pat. No. 12,144,679.

(Continued)

(30) Foreign Application Priority Data

Apr. 20, 2022    (EP) ..................................... 22169024

(51) Int. Cl.
| | |
|---|---|
| A61B 8/00 | (2006.01) |
| A61B 8/06 | (2006.01) |
| A61B 8/12 | (2006.01) |

(52) U.S. Cl.
CPC .............. *A61B 8/4254* (2013.01); *A61B 8/06* (2013.01); *A61B 8/12* (2013.01); *A61B 8/488* (2013.01); *A61B 8/5207* (2013.01)

(58) Field of Classification Search
CPC ........... A61B 8/4254; A61B 8/06; A61B 8/12; A61B 8/488; A61B 8/5207; A61B 8/463; A61B 8/0891; G01S 15/8981
See application file for complete search history.

(56) References Cited

U.S. PATENT DOCUMENTS

| | | |
|---|---|---|
| 4,760,737 A | 8/1988 | Kupperman |
| 4,941,474 A | 7/1990 | Pratt |

(Continued)

OTHER PUBLICATIONS

Van De Hoef, Tim P. et al."Fundamentals in clinical coronary physiology: why coronary flow is more important than coronary pressure", European Heart Journal, vol. 36, pp. 3312-3319, 2015.

(Continued)

*Primary Examiner* — Bo Joseph Peng

(57) ABSTRACT

An intraluminal sensing system is provided, which includes an intraluminal device. The intraluminal device includes a flexible elongate member that can be positioned within a body lumen of a patient, and an ultrasound sensor at a distal portion of the flexible elongate member and configured to emit an ultrasound pulse in a longitudinal direction and to receive ultrasound echoes from the pulse. The system also includes a processor circuit in communication with the ultrasound sensor. The processor circuit is configured to compute a velocity spectrum of particles moving within the body lumen based on the received ultrasound echoes and, based on the velocity spectrum, compute a skew index indicative of a position or alignment of the ultrasound sensor within the body lumen. The processor circuit is also configured to output an indication of the skew index.

11 Claims, 21 Drawing Sheets

Related U.S. Application Data

(60) Provisional application No. 63/297,704, filed on Jan. 8, 2022.

(56) References Cited

U.S. PATENT DOCUMENTS

| | | | | |
|---|---|---|---|---|
| 5,600,073 | A | 2/1997 | Hill | |
| 5,741,980 | A | 4/1998 | Hill | |
| 5,928,153 | A | 7/1999 | Chiang | |
| 10,482,582 | B2 | 11/2019 | Courtney | |
| 2002/0151795 | A1* | 10/2002 | Palti | A61B 8/06 |
| | | | | 600/455 |
| 2007/0167757 | A1 | 7/2007 | Haimerl | |
| 2008/0210016 | A1 | 9/2008 | Zwirn | |
| 2009/0005675 | A1* | 1/2009 | Grunwald | A61B 5/349 |
| | | | | 600/467 |
| 2009/0024037 | A1* | 1/2009 | Baba | A61B 8/06 |
| | | | | 600/454 |
| 2010/0137717 | A1* | 6/2010 | Strand | G01S 15/8979 |
| | | | | 382/128 |
| 2017/0325770 | A1* | 11/2017 | Edic | A61B 6/503 |
| 2020/0022676 | A1 | 1/2020 | Hendriks | |

OTHER PUBLICATIONS

Gould, K. Lance "Pressure-flow characteristics of coronary stenosis in unsedated dogs at rest and during coronary vasodilation", Circulation Research, vol. 43, No., Aug. 1978.

Echavarria-Pinto, Mauro et al "Disturbed coronary hemodynamics in vessels with intermediate stenosis evaluated with fractional flow reserve: a combined analysis of epicardial and microcirculatory involvement in ischemic heart disease", Circulation, 2013.

Van De Hoef, Tim P. et al, "Physiological basis and long-term clinical outcome of discordance between fractional flow reserve and coronary flow velocity reserve in coronary stenoses of intermediate severity", Circulation Cardiovascular Intervention, 2014.

Van De Hoef, Tim P. et al, "Coronary pressure-flow relations as basis for the understanding of coronary physiology", Journal of Moclecular and Cellular Cardiology, vol. 52, 2012, pp. 786-793.

Barbato, Emanuele et al, "Validation of coronary flow reserve measurements by thermodilution in clinical practice", European Heart Journal, vol. 25, 2004, pp. 219-223.

De Bruyne, Bernard et al "Coronary thermodilution to assess flow reserve: experimental validation", Circulation, 2001.

Buchi, Martin et al "Position Control of Intravascular Doppler Guidewire: Concept of a Tracking Indicator and Its Clinical Implications", Catheterization and Cardiovascular Diagnosis, vol. 44, pp. 28-33, 1998.

Fearon, William F. et al "Novel index for invasively assessing the coronary microcirculation", Circulation, 2003.

Jarvis, K.A. et al "Accuracy of the thermodilution method in estimating high flow—an in vitro study", Journal of Veterinary Anesthesia, vol. 19, pp. 41-45, 1992.

Julien I.E. Hoffman, "Maximal coronary flow and the concept of coronary vascular reserve", Circulation, vol. 70, Aug. 1984.

Gould, K. Lance et al "Physiologic basis for assessing critical coronary stenosis. Instantaneous flow response and regional distribution during coronary hyperemia as measures of coronary flow reserve", The American Journal of Cardiology, vol. 33, Issue 1, Jan. 1974, pp. 87-94.

Meuwissen, Siebes et al, "Role of fractional and coronary flow reserve in clinical decision making in intermediate coronary lesions", Interventional Cardiology, vol. 1, No. 2, 2009, pp. 237-255.

Echavarria-Pinto, Mauro et al, "Facing the complexity of ischaemic heart disease with intracoronary pressure and flow measurements: beyond fractional flow reserve interrogation of the coronary circulation", Current Opinion in Cardiology, vol. 29, No. 6, pp. 564-570, 2014.

Meuwissen, Martijn et al "Hyperemic stenosis resistance index for evaluation of functional coronary lesion severity", Circulation, 2002.

Van De Hoef, Tim P. et al "Diagnostic accuracy of combined intracoronary pressure and flow velocity information during baseline conditions: adenosine-free assessment of functional coronary lesion severity", Cardiovascular Intervention, 2012.

Buchi, M. et al Measurement of flow velocity in the coronary circulation: requirements and pitfalls. Seminars in Interventional Cardiology, vol. 3, No. 1, 1998, pp. 45-50.

* cited by examiner

PHYSIOLOGY SENSING INTRALUMINAL DEVICE WITH INDEX FOR SPECTRAL FLOW ASSESSMENT, AND ASSOCIATED DEVICES, SYSTEMS, AND METHODS

CROSS-REFERENCE TO RELATED APPLICATIONS

This application is a continuation of U.S. application Ser. No. 18/094,371, filed Jan. 8, 2023, now U.S. Pat. No. 12,144,679, which claims priority to and the benefit of U.S. Provisional Application No. 63/297,704, filed Jan. 8, 2022. This application claims priority to European Application No. 22169024.1, filed Apr. 20, 2022. Each of these applications is incorporated by reference herein in its entirety.

TECHNICAL FIELD

The subject matter described herein relates to devices and methods for improving sensor positioning and measurement quality for physiology sensing intraluminal devices. This intraluminal measurement system has particular but not exclusive utility for intravascular catheters and guidewires.

BACKGROUND

Coronary artery disease (CAD) is among the world's leading causes of death. To address this problem, image guided therapy (IGT) makes use of a wide variety of imaging modalities (e.g., coronary angiography) as well as in-body diagnostic devices (e.g. pressure-sensing guidewires or intravascular ultrasound catheters). Small-diameter medical devices such as intraluminal (e.g., intravascular) catheters and guidewires may incorporate sensors (e.g., pressure, temperature, flow, or imaging sensors) whose power and communications occur through electrical and/or optical conductor bundles.

Flow reserve is a concept that estimates the extent flow can increase over a resting baseline. Fractional Flow Reserve (FFR) and instant wave-Free Ratio (iFR) are indices that estimate competency of a coronary epicardial artery with regard to flow reserve. They rely on pressure as a surrogate for flow. FFR and iFR are currently used as the go-to standard to identify candidates for percutaneous coronary intervention (PCI). A significant percentage of the population with microvascular coronary artery disease (CAD), predominantly women, does not qualify as a PCI candidate using pressure based measurements because their disease is primarily located in the coronary microvasculature, rather than in the large coronary vessels.

Coronary Flow Reserve (CFR) uses velocity as the basis of its measurement. CFR is an index that covers both epicardial and microvascular arterial domains. Additionally, other indices, e.g., Microvascular Resistance Index (MRI), Hyperemic Microvascular Resistence (HMR), and Index of Microcirculatory Resistance (IMR), measure only the microvascular contribution to CAD. These indices rely on direct measurement of flow, as well as pressure. Physicians need a tool to identify and treat microvascular disease.

A guidewire configured for Doppler flow velocity measurements may be used to assess flow. However, measurement of flow velocity within a coronary artery using Doppler technology faces the obstacle of aligning the transducer along the lumen axis, whereas pressure-based measurements do not rely on a particular orientation. Existing intravascular systems for measuring blood flow parameters may in some cases be burdensome to learn and use, and may for example involve the memorization and interpretation of audio signals generated from the Doppler waveforms. Such burdens may for example apply to interventional cardiologists who perform intravascular flow measurements to diagnose microvascular disease with Doppler sensor positioning and signal optimization. Limitations of the current technology limit the usability of current systems, which may ultimately contribute to physician frustration and lack of adoption. It may also extend overall procedure duration, which increases the costs of care.

The information included in this Background section of the specification, including any references cited herein and any description or discussion thereof, is included for technical reference purposes only and is not to be regarded as subject matter by which the scope of the disclosure is to be bound.

SUMMARY

A blood flow velocity sensing guidewire can be used for example to assess Non-Obstructive Coronary Artery Disease (NOCAD) and Micro Vascular Disease (MVD). The present disclosure adds novel capabilities to such flow sensing systems, including a spectral flow assessment index or skew index that can serve as a guide for the optimal placement of a flow transducer within a coronary artery. In some cases, the skew index may be largely or wholly independent of heart rate and velocity amplitude, and can therefore provide placement feedback directly to a user or to an automatic electro-mechanical device responsible for aligning the transducer. The index provides an objective and repeatable indicator of alignment and signal quality, requires very little training, and is not subject to interpretation.

Such methods may be useful in blood flow velocity measurements, blood flow measurements, Doppler ultrasound measurements, positioning, and signal optimization. The flow sensing systems, devices, and methods described herein have particular, but not exclusive, utility for intraluminal medical catheters and guidewires.

The present application advantageously provides devices, systems, and methods to simplify the process of obtaining direct flow measurements, to provide feedback to identify the most optimal transducer alignment, and in some cases to correct the flow measurements obtained from a misaligned transducer. Flow measurements' reliance on alignment is advantageously addressed in the present application, thus allowing for flow to be directly implemented (rather than using pressure as a substitute).

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an intraluminal sensing system which includes an intraluminal device. The intraluminal device includes: a flexible elongate member configured to be positioned in a longitudinal direction within a body lumen of a patient, and an ultrasound sensor disposed at a distal portion of the flexible elongate member and configured to emit an ultrasound pulse in substantially the longitudinal direction while positioned within the body lumen and to receive ultrasound echoes from the ultrasound pulse. The intraluminal sensing system also includes a processor circuit in communication with the ultrasound sensor and configured to: compute a velocity spectrum of particles moving within the body lumen based on the received ultrasound echoes; based on the velocity spectrum, compute a skew index indicative of a position or alignment of the ultrasound sensor within the body lumen; and output an indication of the skew index. Other embodiments of this aspect include corresponding computer systems, apparatus, and computer programs recorded on one or more computer storage devices, each configured to perform the actions of the methods.

Implementations may include one or more of the following features. In some embodiments, the processor circuit is further configured to determine whether the skew index falls within a pre-determined range indicative of a signal quality of the received ultrasound echoes. In some embodiments, the processor circuit is further configured to display the indication of the skew index on a display device in communication with the processor circuit. In some embodiments, the indication is numerical. In some embodiments, the indication is graphical. In some embodiments, the processor circuit is further configured to generate an audible indication of the skew index, where the audible indication is different from a doppler chirp. In some embodiments, the processor circuit is further configured to: determine which components of the velocity spectrum result from wall motion of the body lumen; and remove from the velocity spectrum those components that result from wall motion of the body lumen. In some embodiments, determining which velocities of the velocity spectrum result from wall motion of the body lumen includes at least one of identifying velocity measurements below a specified threshold velocity or identifying velocity measurements with a pattern recognition algorithm. In some embodiments, computing the skew index involves a time gate or time average. In some embodiments, computing the velocity spectrum includes computing a plurality of velocity spectra at a plurality of sampling depths, and where computing the skew index includes computing a respective skew index for each sampling depth of the plurality of sampling depths. In some embodiments, the processor circuit is further configured to display, on a display device in communication with the processor circuit, a graph of the respective skew indices vs. the plurality of sampling depths. In some embodiments, the processor circuit is further configured to compute a numerical parameter indicative of a variability of the respective skew indices. In some embodiments, the processor circuit is further configured to display, on a display device in communication with the processor circuit, a visual representation of the numerical parameter. In some embodiments, the numerical parameter is a standard deviation or a min-max range. In some embodiments, the processor circuit is further configured to determine whether the numerical parameter falls within a pre-determined range indicative of a signal quality of the received ultrasound echoes. In some embodiments, the processor circuit is further configured to, based on the skew index, adjust a threshold parameter that is used to discriminate signal from noise in the ultrasound echoes. Implementations of the described techniques may include hardware, a method or process, or computer software on a computer-accessible medium.

One general aspect includes a method for intraluminal sensing. The method includes, with an ultrasound sensor disposed at a distal portion of a flexible elongate member positioned within a body lumen of a patient: emitting an ultrasound pulse in a substantially longitudinal direction, and receiving ultrasound echoes from the ultrasound pulse. The method also includes, with a processor circuit in communication with the ultrasound sensor: computing a velocity spectrum of particles moving within the body lumen based on the received ultrasound echoes; based on the velocity spectrum, computing a skew index indicative of a position or alignment of the sensing element within the body lumen; and outputting an indication of the skew index. Other embodiments of this aspect include corresponding computer systems, apparatus, and computer programs recorded on one or more computer storage devices, each configured to perform the actions of the methods.

One general aspect includes an intraluminal sensing system which includes a sensing guidewire including: a flexible elongate member configured to be positioned in a longitudinal direction within a blood vessel of a patient, and an intravascular ultrasound sensor disposed at a distal portion of the flexible elongate member and configured to emit an ultrasound pulse in substantially the longitudinal direction while positioned within the blood vessel and to receive Doppler-shifted echoes from the ultrasound pulse. The intraluminal sensing system also includes a processor circuit in communication with the intravascular ultrasound sensor and configured to: compute a velocity spectrum of particles moving within the blood vessel based on the received Doppler-shifted echoes; based on the velocity spectrum, compute a skew index indicative of a position or alignment of the intravascular ultrasound sensor within the blood vessel; and determine whether the skew index falls within a pre-determined range indicative of a signal quality of the received ultrasound echoes; or display an indication of the skew index on a display device in communication with the processor circuit. Other embodiments of this aspect include corresponding computer systems, apparatus, and computer programs recorded on one or more computer storage devices, each configured to perform the actions of the methods.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the flow measurement system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
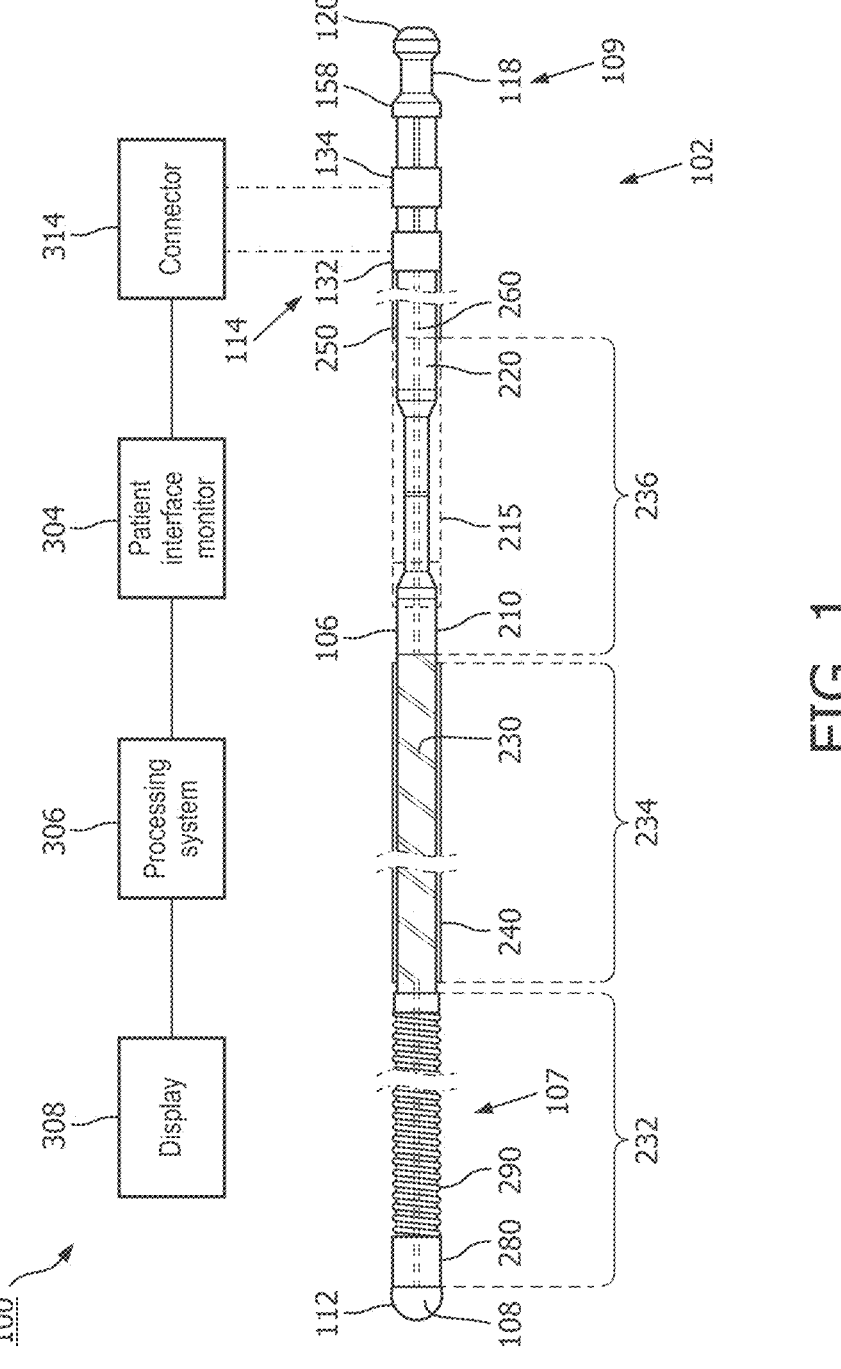
FIG. 1 is a diagrammatic side view of an intravascular sensing system that includes an intravascular device comprising an a multi-filar electrical conductor bundle, according to aspects of the present disclosure.

Coronary artery disease (CAD) is among the world's leading causes of death. To address this problem, Philips Image Guided Therapy (IGT) has a strong portfolio in imaging systems (for e.g. coronary angiography) as well as in-body diagnostic devices (e.g. pressure-sensing guidewires or intravascular ultrasound catheters). One such diagnostic device is the blood flow velocity sensing guidewire, which can be used for example to assess Non-Obstructive Coronary Artery Disease (NOCAD) and Micro Vascular Disease (MVD). These guidewires are equipped with a single-element ultrasound transducer that is located at its tip. The transducer can emit ultrasound waves in a forward-looking direction and receive the corresponding pulse-echo signals. By pulsed-wave (PW) Doppler analysis, the blood velocity distribution in a specific sampling volume can be deduced.

Clinical outcomes of interventions may be improved when they are based on translesional physiology measurements. Rather than relying on angiography, modern coronary assessment relies on physiology and the measurement of flow. Historically, flow measurements preceded pressure-based measurements for coronary assessment. However, clinically, it was more efficient to substitute pressure for flow. The downside of this substitution is the omission of the microvascular contribution in the coronary assessment. While it has been demonstrated that epicardial measurements (FFR, iFR) increased the reliance on physiology, it has been further demonstrated that epicardial measurements are not enough to get the whole picture. When interpreting the diagnostic characteristics of FFR, it can be important to acknowledge FFR is derived as a surrogate measure of coronary flow impairment, and is not the same as direct measurements of coronary flow, which may be critical determinants of conditions such as myocardial ischemia.

Flow measurements can be acquired using thermodilution, but there is speculation that the accuracy of the thermodilution method is compromised in pulsatile flow.

Multiple saline injections may also be needed for thermo-dilution, which may be suboptimal with respect to workflow efficiency. The concept of flow measurement has been demonstrated to provide significant understanding to the assessment of coronary stenosis and the application of FFR.

The present disclosure provides an index for spectral flow assessment that can serve as a guide for the optimal placement of a flow transducer within a coronary artery. In some cases, the index may be largely or wholly independent of heart rate and velocity amplitude. The index can therefore provide placement feedback directly to a user or to an automatic electro-mechanical device responsible for aligning the transducer. Currently, the user relies on subjective interpretation of the audio Doppler signal and visual spectrum to determine alignment. Conversely, the index disclosed herein provides an objective and repeatable indicator of alignment and signal quality. Both the audio signal and visual spectrum techniques require training and practice for reliable results. The disclosed index requires very little training and is not subject to interpretation.

The concept involves determining the alignment via the shape of the histogram of the velocity spectrum-a quality that can be described for practical purposes with a single dimensionless index. Different embodiments are also disclosed to address issues such as 1) the phase to best determine the index, 2) how to deal with wall motion, 3) how to utilize index variation in time and 4) employing variation in sampling depth. In case of a straight tube and steady flow the velocity distribution is shaped as a parabola or Poiseuille (see FIG. 7). In case of good alignment, most of the velocities that are measured will be in the high range, resulting in a velocity histogram which is skewed to the higher velocities.

The present disclosure aids substantially in the measurement of intravascular flow, by improving sensor positioning and the quality of flow parameter measurements. Implemented on an ultrasound guidewire in communication with a processor, the flow measurement system disclosed herein provides practical guidewire positioning information and, in some cases, automatic improvement or correction of flow measurements. This augmented flow measurement system transforms a tedious, knowledge-intensive guidewire placement process into a process that can be performed with less a priori knowledge and training, without the normally routine need to take multiple measurements or interpret audible Doppler chirps. This unconventional approach improves the functioning of the flow-sensing guidewire, by providing improved guidance and outputs to the clinician.

Aspects of the present disclosure can include features described in App. No. 63/297,703, filed Jan. 8, 2022, and titled "Physiology Sensing Intraluminal Device with Positioning Guidance and Associated Devices, Systems, and Methods", the entirety of which is hereby incorporated by reference herein.

The outputs of the methods disclosed herein may be viewable on a display, and the methods may be operated by a control process executing on a processor that accepts user inputs from a keyboard, mouse, touchscreen interface, speech or gesture control, and that is in communication with one or more sensors. In that regard, the control process performs certain specific operations in response to different inputs or selections made at different times. Certain structures, functions, and operations of the processor, display, sensors, and user input systems are known in the art, while others are recited herein to enable novel features or aspects of the present disclosure with particularity.

These descriptions are provided for exemplary purposes only and should not be considered to limit the scope of the flow measurement system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. Additionally, while the description below may refer to blood vessels, it will be understood that the present disclosure is not limited to such applications. For example, the devices, systems, and methods described herein may be used in any body chamber or body lumen, including an esophagus, veins, arteries, intestines, ventricles, atria, or any other body lumen and/or chamber. For the sake of brevity, however, the numerous iterations of these combinations will not be described separately.

FIG. 1 is a diagrammatic side view of an intravascular sensing system 100 that includes an intravascular device 102 comprising a multi-filar electrical conductor bundle 230, according to aspects of the present disclosure. The intravascular device 102 can be an intravascular guidewire sized and shaped for positioning within a vessel of a patient. The intravascular device 102 can include a distal tip 108 and a sensing component 112. The sensing component 112 can be an electronic, electromechanical, mechanical, optical, and/or other suitable type of sensor. For example, the electronic component 112 can be a flow sensor configured to measure the velocity of blood flow within a blood vessel of a patient, a pressure sensor configured to measure a pressure of blood flowing within the vessel, or another type of sensor including but not limited to a temperature or imaging sensor. For example, flow data obtained by a flow sensor can be used to calculate physiological variables such as coronary flow reserve (CFR). Pressure data obtained by a pressure sensor may for example be used to calculate a physiological pressure ratio (e.g., FFR, iFR, Pd/Pa, or any other suitable pressure ratio). An imaging sensor may include an intravascular ultrasound (IVUS), intracardiac echocardiography (ICE), optical coherence tomography (OCT), or intravascular photoacoustic (IVPA) imaging sensor. For example, the imaging sensor can include one or more ultrasound transducer elements, including an array of ultrasound transducer elements.

The intravascular device 102 includes a flexible elongate member 106. The electronic component 112 is disposed at the distal portion 107 of the flexible elongate member 106. The electronic component 112 can be mounted at the distal portion 107 within a housing 280 in some embodiments. A flexible tip coil 290 extends distally from the housing 280 at the distal portion 107 of the flexible elongate member 106. A connection portion 114 located at a proximal end of the flexible elongate member 106 includes conductive portions 132, 134. In some embodiments, the conductive portions 132, 134 can be conductive ink that is printed and/or deposited around the connection portion 114 of the flexible elongate member 106. In some embodiments, the conductive portions 132, 134 are conductive, metallic rings that are positioned around the flexible elongate member. A locking section is formed by collar 118 and knob 120 are disposed at the proximal portion 109 of the flexible elongate member 106.

The intravascular device 102 in FIG. 1 includes a distal core wire 210 and a proximal core wire 220. The distal core 210 and the proximal core 220 are metallic components forming part of the body of the intravascular device 102. For example, the distal core 210 and the proximal core 220 are flexible metallic rods that provide structure for the flexible elongate member 106. The diameter of the distal core 210 and the proximal core 220 can vary along its length. A joint between the distal core 210 and proximal core 220 is surrounded and contained by a hypotube 215.

In some embodiments, the intravascular device 102 comprises a distal assembly and a proximal assembly that are electrically and mechanically joined together, which provides for electrical communication between the electronic component 112 and the conductive portions 132, 134. For example, flow data obtained by the electronic component 112 (in this example, electronic component 112 is a flow sensor) can be transmitted to the conductive portions 132, 134. Control signals (e.g., operating voltage, start/stop commands, etc.) from a processor system 306 in communication with the intravascular device 102 can be transmitted to the electronic component 112 via a connector 314 that is attached to the conductive portions 132, 134. The distal subassembly can include the distal core 210. The distal subassembly can also include the electronic component 112, the multi-filar conductor bundle 230, and/or one or more layers of insulative polymer/plastic 240 surrounding the conductive members 230 and the core 210. For example, the polymer/plastic layer(s) can insulate and protect the conductive members of the multi-filar cable or conductor bundle 230. The proximal subassembly can include the proximal core 220. The proximal subassembly can also include one or more layers of polymer layer(s) 250 (hereinafter polymer layer 250) surrounding the proximal core 220 and/or conductive ribbons 260 embedded within the one or more insulative and/or protective polymer layer(s) 250. In some embodiments, the proximal subassembly and the distal subassembly can be separately manufactured. During the assembly process for the intravascular device 102, the proximal subassembly and the distal subassembly can be electrically and mechanically joined together. As used herein, flexible elongate member can refer to one or more components along the entire length of the intravascular device 102, one or more components of the proximal subassembly (e.g., including the proximal core 220, etc.), and/or one or more components the distal subassembly 210 (e.g., including the distal core 210, etc.). The joint between the proximal core 220 and distal core 210 is surrounded by the hypotube 215.

In various embodiments, the intravascular device 102 can include one, two, three, or more core wires extending along its length. For example, in one embodiment, a single core wire extends substantially along the entire length of the flexible elongate member 106. In such embodiments, a locking section 118 and a section 120 can be integrally formed at the proximal portion of the single core wire. The electronic component 112 can be secured at the distal portion of the single core wire. In other embodiments, such as the embodiment illustrated in FIG. 1, the locking section 118 and the section 120 can be integrally formed at the proximal portion of the proximal core 220. The electronic component 112 can be secured at the distal portion of the distal core 210. The intravascular device 102 includes one or more conductive members in a multi-filar conductor bundle 230 in communication with the electronic component 112. For example, the conductor bundle 230 can include one or more electrical wires that are directly in communication with the electronic component 112. In some instances, the conductive members 230 are electrically and mechanically coupled to the electronic component 112 by, e.g., soldering. In some instances, the conductor bundle 230 comprises two or three electrical wires (e.g., a bifilar cable or a trifilar cable). An individual electrical wire can include a bare metallic conductor, or a metallic conductor surrounded by one or more insulating layers. The multi-filar conductor bundle 230 can extend along a length of the distal core 210. For example, at least a portion of the conductive members 230 can be helically, or spirally, wrapped around an entire length of the distal core 210, or a portion of the length of the distal core 210.

The intravascular device 102 includes one or more conductive ribbons 260 at the proximal portion of the flexible elongate member 106. The conductive ribbons 260 are embedded within polymer layer(s) 250. The conductive ribbons 260 are directly in communication with the conductive portions 132 and/or 134. In some instances, the multi-filar conductor bundle 230 is electrically and mechanically coupled to the electronic component 112 by, e.g., soldering. In some instances, the conductive portions 132 and/or 134 comprise conductive ink (e.g., metallic nano-ink, such as silver or gold nano-ink) that is deposited or printed directed over the conductive ribbons 260.

As described herein, electrical communication between the conductive members 230 and the conductive ribbons 260 can be established at the connection portion 114 of the flexible elongate member 106. By establishing electrical communication between the conductor bundle 230 and the conductive ribbons 260, the conductive portions 132, 134 can be in electrically communication with the electronic component 112.

In some embodiments represented by FIG. 1, intravascular device 102 includes a locking section 118 and a section 120. To form locking section 118, a machining process is necessary to remove polymer layer 250 and conductive ribbons 260 in locking section 118 and to shape proximal core 220 in locking section 118 to the desired shape. As shown in FIG. 1, locking section 118 includes a reduced diameter while section 120 has a diameter substantially similar to that of proximal core 220 in the connection portion 114. In some instances, because the machining process removes conductive ribbons in locking section 118, proximal ends of the conductive ribbons 260 would be exposed to moisture and/or liquids, such as blood, saline solutions, disinfectants, and/or enzyme cleaner solutions, an insulation layer 158 is formed over the proximal end portion of the connection portion 114 to insulate the exposed conductive ribbons.

In some embodiments, a connector 314 provides electrical connectivity between the conductive portions 132, 134 and a patient interface module or patient interface monitor 304. The patient interface module (PIM) 304 may in some cases connect to a console or processing system 306, which includes or is in communication with a display 308. In some embodiments, the patient interface module 304 includes signal processing circuitry, such as an analog-to-digital converter (ADC), analog and/or digital filters, signal conditioning circuitry, and any other suitable signal processing circuitry for processing the signals provided by the electronic component 112 for use by the processing system 306.

The system 100 may be deployed in a catheterization laboratory having a control room. The processing system 306 may be located in the control room. Optionally, the processing system 306 may be located elsewhere, such as in the catheterization laboratory itself. The catheterization laboratory may include a sterile field while its associated control room may or may not be sterile depending on the procedure to be performed and/or on the health care facility. In some embodiments, device 102 may be controlled from a remote location such as the control room, such than an operator is not required to be in close proximity to the patient.

The intraluminal device 102, PIM 304, and display 308 may be communicatively coupled directly or indirectly to the processing system 306. These elements may be communicatively coupled to the medical processing system 306 via a wired connection such as a standard copper multi-filar conductor bundle 230. The processing system 306 may be communicatively coupled to one or more data networks, e.g., a TCP/IP-based local area network (LAN). In other embodiments, different protocols may be utilized such as Synchronous Optical Networking (SONET). In some cases, the processing system 306 may be communicatively coupled to a wide area network (WAN).

The PIM 304 transfers the received signals to the processing system 306 where the information is processed and displayed on the display 308. The console or processing system 306 can include a processor and a memory. The processing system 306 may be operable to facilitate the features of the intravascular sensing system 100 described herein. For example, the processor can execute computer readable instructions stored on the non-transitory tangible computer readable medium.

The PIM 304 facilitates communication of signals between the processing system 306 and the intraluminal device 102. In some embodiments, the PIM 304 performs preliminary processing of data prior to relaying the data to the processing system 306. In examples of such embodiments, the PIM 304 performs amplification, filtering, and/or aggregating of the data. In an embodiment, the PIM 304 also supplies high- and low-voltage DC power to support operation of the intraluminal device 102 via the multi-filar conductor bundle 230.

The multi-filar cable or transmission line bundle 230 can include a plurality of conductors, including one, two, three, four, five, six, seven, or more conductors. The multi-filar conductor bundle 230 can be positioned along the exterior of the distal core 210. The multi-filar conductor bundle 230 and the distal core 210 can be overcoated with an insulative and/or protective polymer 240. In the example shown in FIG. 1, the multi-filar conductor bundle 230 includes two straight portions 232 and 236, where the multi-filar conductor bundle 230 extends linearly and parallel to a longitudinal axis of the flexible elongate member 106 on the exterior of the distal core 210, and a helical or spiral portion 234, where the multi-filar conductor bundle 230 is wrapped around the exterior of the distal core 210. In some embodiments, the multi-filar conductor bundle 230 only includes a straight portion or only includes a helical or spiral portion. In general, the multi-filar conductor bundle 230 can extend in a linear, wrapped, non-linear, or non-wrapped manner, or any combination thereof. Communication, if any, along the multi-filar conductor bundle 230 may be through numerous methods or protocols, including serial, parallel, and otherwise, wherein one or more filars of the bundle 230 carry signals. One or more filars of the multi-filar conductor bundle 230 may also carry direct current (DC) power, alternating current (AC) power, or serve as an electrical ground connection.

The display or monitor 308 may be a display device such as a computer monitor, a touch-screen display, a television screen, or any other suitable type of display. The monitor 308 may be used to display selectable prompts, instructions, and visualizations of imaging data to a user. In some embodiments, the monitor 308 may be used to provide a procedure-specific workflow to a user to complete an intraluminal imaging procedure.

Before continuing, it should be noted that the examples described above are provided for purposes of illustration, and are not intended to be limiting. Other devices and/or device configurations may be utilized to carry out the operations described herein.

Figure 2:
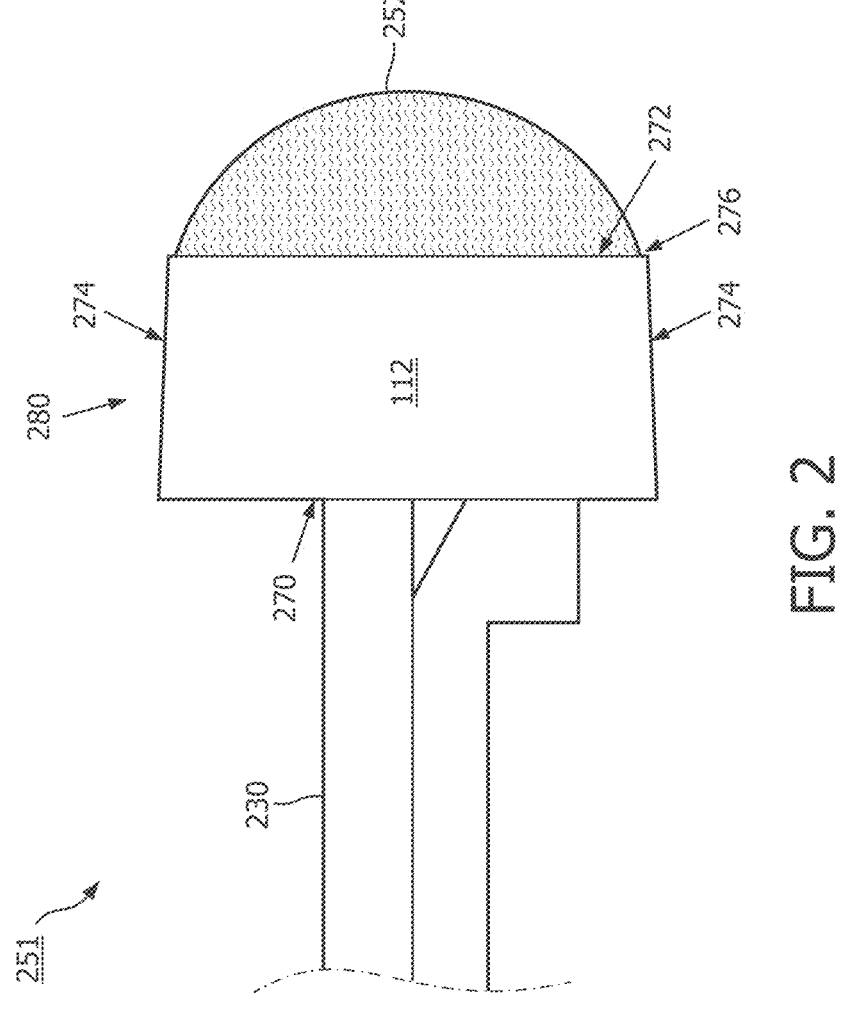
FIG. 2 is side cross sectional view of an example electronic component of an intravascular device, in accordance with aspects of the present disclosure.

FIG. 2 is a diagrammatic cross-sectional view of an example sensor assembly 251, which may for example be included in the intravascular device 102 of FIG. 1. More specifically, FIG. 2 illustrates a sensor assembly 251 that includes a sensing component 112, a housing 280, and an acoustic matching layer 252. As indicated by the positions of the sensing component 112 and the housing 280 illustrated in FIG. 1, the sensor assembly 251 may be included in a distal portion of the intravascular device 102 such that the surface 272 of the sensing component 112 faces distally.

As illustrated in FIG. 2, the sensing component 112 is positioned within the housing 280 and includes a proximal surface 270, an opposite, distal surface 272, and a side surface 274. In some embodiments, one or more of the proximal surface 270, the distal surface 272, or the side surface 274 may be coated in an insulating layer 276. The insulating layer 276 may be formed from parylene, which may be deposited on the one or more surfaces, for example. The insulating layer 276 may additionally or alternatively be formed from any other suitable insulating material. In some embodiments, the insulating layer 276 may prevent a short (e.g., an electrical failure), which may otherwise be caused by contact between a conductive portion of the sensing component 112 and the housing 280, which may be formed with a metal. As used herein, references to the distal surface 272 encompass the insulating layer 276 in embodiments where a distal end of the sensing component 112 is covered by the insulating layer 276, references to the proximal surface 270 encompass the insulating layer in embodiments where a proximal end of the sensing component 112 is covered by the insulating layer 276, and references to the side surface 274 encompass the insulating layer in embodiments where the side of the sensing component 112 is covered by the insulating layer 276 unless indicated otherwise.

In some embodiments, the sensing component 112 may include a transducer element, such as an ultrasound transducer element on the distal surface 272 such that the transducer element faces distally and may be used by the sensing component 112 to obtain sensor data corresponding to a structure distal of the sensing component 112. The sensing component 112 may additionally or alternatively include a transducer element on the proximal surface 270 such that the transducer faces proximally and may be used to obtain sensor data corresponding to a structure proximal of the sensing component. A transducer element may additionally or alternatively be positioned on a side surface 274 (e.g., on a perimeter or circumference) of the sensing component 112 in some embodiments.

As further illustrated, the sensing component 112 is coupled to the multi-filar conductor bundle 230, and at least a portion (e.g., a distal portion) of the multi-filar conductor bundle 230 are extends through the housing 280. In some embodiments, the multi-filar conductor bundle 230 and the sensing component 112 may be physically (e.g., mechanically) coupled. Further, one or more filars (e.g., conductive members) of the multi-filar conductor bundle 230 may electrically couple to (e.g., be in electrical communication) with the sensing component 112. In particular, one or more filars of the multi-filar conductor bundle 230 may couple to an element, such as a transducer (e.g., an ultrasound transducer), of the sensing component 112 and may provide power, control signals, an electrical ground or signal return, and/or the like to the element. As described above, such an element may be positioned on the distal surface 272 of the sensor. In that regard, in some embodiments, one or more filars of the multi-filar conductor bundle 230 may extend through a cutout or hole in the sensing component 112 (e.g., in at least the proximal surface 270) to establish electrical communication with an element on the distal surface 272 of the sensor. Filars may additionally or alternatively wrap around the side surface 274 to establish electrical communication with the element on the distal surface 272. Moreover, in some embodiments, filars of the multi-filar conductor bundle 230 may terminate at and/or electrically couple to the proximal surface 270 (e.g., to an element on the proximal surface 270) of the sensing component 112. Further, in some embodiments, a subset of the filars of the multi-filar conductor bundle 230 may extend to the distal surface 272 and/or electrically couple to an element at the distal surface 272, while a different subset of the filars may electrically couple to an element at the proximal surface 270, for example.

In some embodiments, the multi-filar conductor bundle 230 may be coated in the insulating layer 276. In some embodiments, for example, the multi-filar conductor bundle 230 and the sensing component 112 may be coupled together in a sub-assembly before being positioned in the housing 280. In such embodiments, the insulating layer 276 may be applied (e.g., coated and/or deposited) onto the entire sub-assembly, resulting in an insulating layer 276 on both the sensing component 112 and the multi-filar conductor bundle 230.

In some embodiments, the acoustic matching layer 252 may be positioned on (e.g., over) the distal surface 272 of the sensing component 112. In particular, the acoustic matching layer 252 may be disposed directly on the sensing component 112, or the acoustic matching layer 252 may be disposed on the insulating layer 276 coating the sensing component 112. Further, the acoustic matching layer 252 may be disposed on a transducer element (e.g., an ultrasound transducer element) positioned on the sensing component (e.g., the distal surface 272) and/or at least a portion of a conductive filar of the multi-filar conductor bundle 230 that is in communication with the transducer element, such as a filar extending through a hole or along a side of the sensing component 112. To that end, the acoustic matching layer 252 may contact and/or at least partially surround the portion of the conductive filar and/or the transducer element. Moreover, the acoustic matching layer 252 may provide acoustic matching to the sensing component 112 (e.g., to an ultrasound transducer of the sensing component 112). For instance, the acoustic matching layer 252 may minimize acoustic impedance mismatch between the ultrasound transducer and a sensed medium, such as a fluid and/or a lumen that the intravascular device 102 is positioned within. In that regard, the acoustic matching layer 252 may be formed from any suitable material, such as a polymer or an adhesive, to provide acoustic matching with the sensing component 112. The portion of the acoustic matching layer 252 positioned on the distal surface 272 may include and/or be formed from the same material as a portion of the acoustic matching layer positioned on the side surface 274 and/or the proximal surface 270. Further, the acoustic matching layer 252 may be applied to the sensing component 112 before or after the sensing component 112 is positioned within the housing 280 during assembly of the sensor assembly 250. In this regard, the portion of the acoustic matching layer 252 positioned on the distal surface 272 and the portion of the acoustic matching layer positioned on the side surface 274 and/or the proximal surface 270 may be included in the sensor assembly 251 in the same or different steps. Further, in addition to the one or more materials the acoustic matching layer 252 is formed from, the acoustic matching layer 252 may provide acoustic matching with the sensing component 112 via one or more dimensions of the acoustic matching layer 252.

In some embodiments, the sensor assembly 251 may include an atraumatic tip, such as the distal tip 108 illustrated in FIG. 1. In some embodiments, the distal tip 108 may include the same material as the acoustic matching layer 252. In some embodiments, the distal tip may include a different material than the acoustic matching layer 252. Additionally or alternatively the distal tip 108 may be formed from one or more layers of materials. The layers may include different materials and/or different configurations (e.g., shape and/or profile, thickness, and/or the like). Further, the distal tip 108 may be arranged to cover the distal surface 272 of the sensing component 112. In some embodiments, the distal tip 108 may also cover a distal end 272 of the housing 280. Moreover, while the distal tip 108 is illustrated as having a domed shape, embodiments are not limited thereto. In this regard, the distal tip 108 may include a flattened profile or any suitable shape. In some embodiments, the entire sensing component 112 may be positioned within (e.g., surrounded by the continuous surface of) the housing 280.

Figures 3A, 3B:
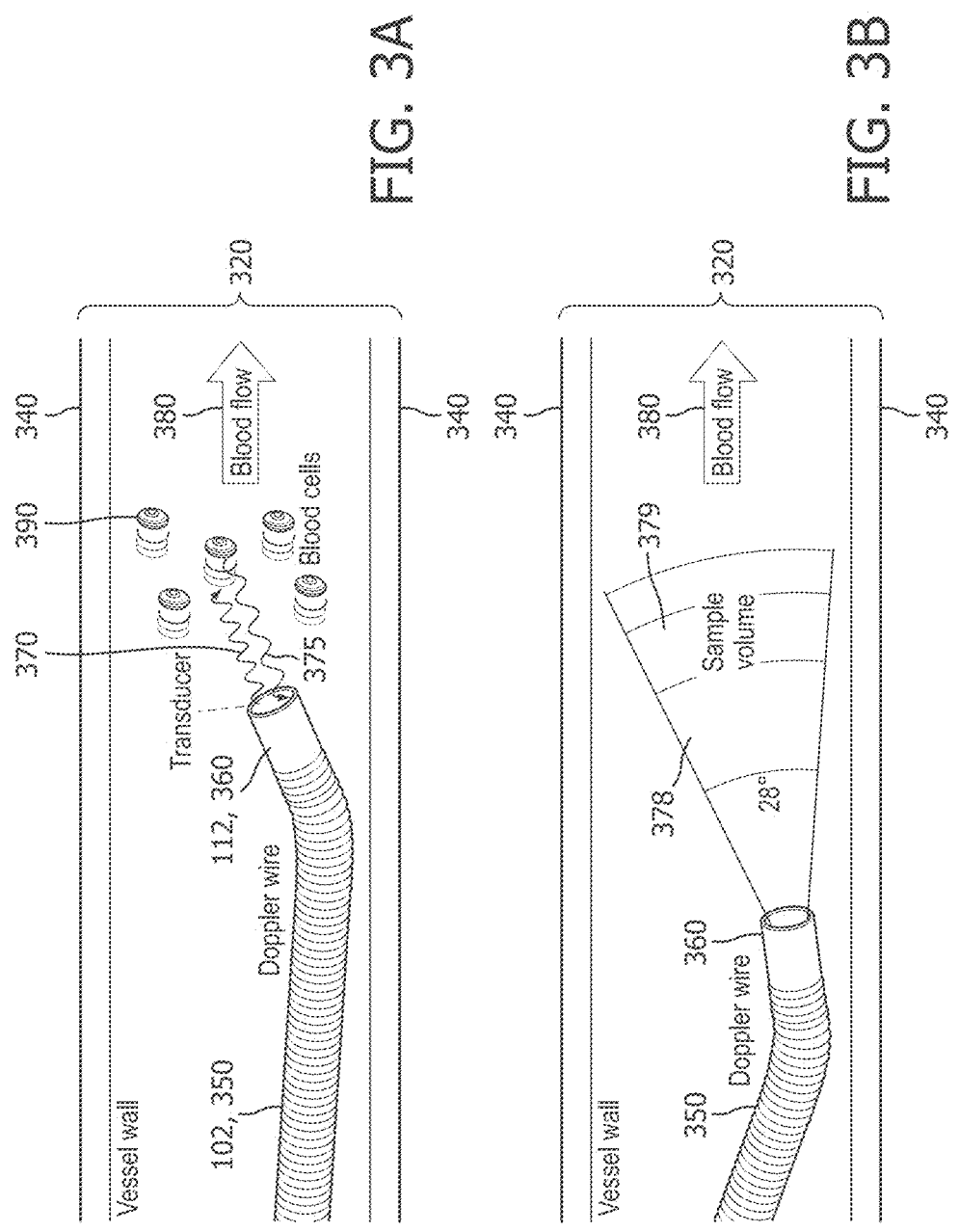
FIG. 3A is a schematic view of an intravascular device during measurement of a flow velocity inside a blood vessel, in accordance with at least one embodiment of the present disclosure.
FIG. 3B is a schematic view of an intravascular device during measurement of a flow velocity inside a blood vessel, in accordance with at least one embodiment of the present disclosure.

FIG. 3A is a schematic view of an intravascular device 102 (e.g., a flow-sensing guidewire 350) during measurement of a flow velocity 380 inside a blood vessel 320 with blood vessel walls 340, in accordance with at least one embodiment of the present disclosure. In the example shown in FIG. 3A, the sensor 112 (e.g., an ultrasound transducer 360) at the tip is shown to emit ultrasound waves 370 that are backscattered as reflections 375 by flowing cells 390 in the blood and sensed by the transducer 360.

FIG. 3B is a schematic view of an intravascular device 102 (e.g., a flow-sensing guidewire 350) during measurement of a flow velocity 380 inside a blood vessel 320 with blood vessel walls 340, in accordance with at least one embodiment of the present disclosure. In the example shown in FIG. 3B, the beam profile or viewing cone 378 of the transducer 360 is schematically shown, along with an example of the sample volume 379 over which the distribution of the flow velocity 380 is measured. This sample volume 379 results from the transducer beam profile or viewing cone 378 as well as the selected measurement distance range, as described below.

Figure 4:
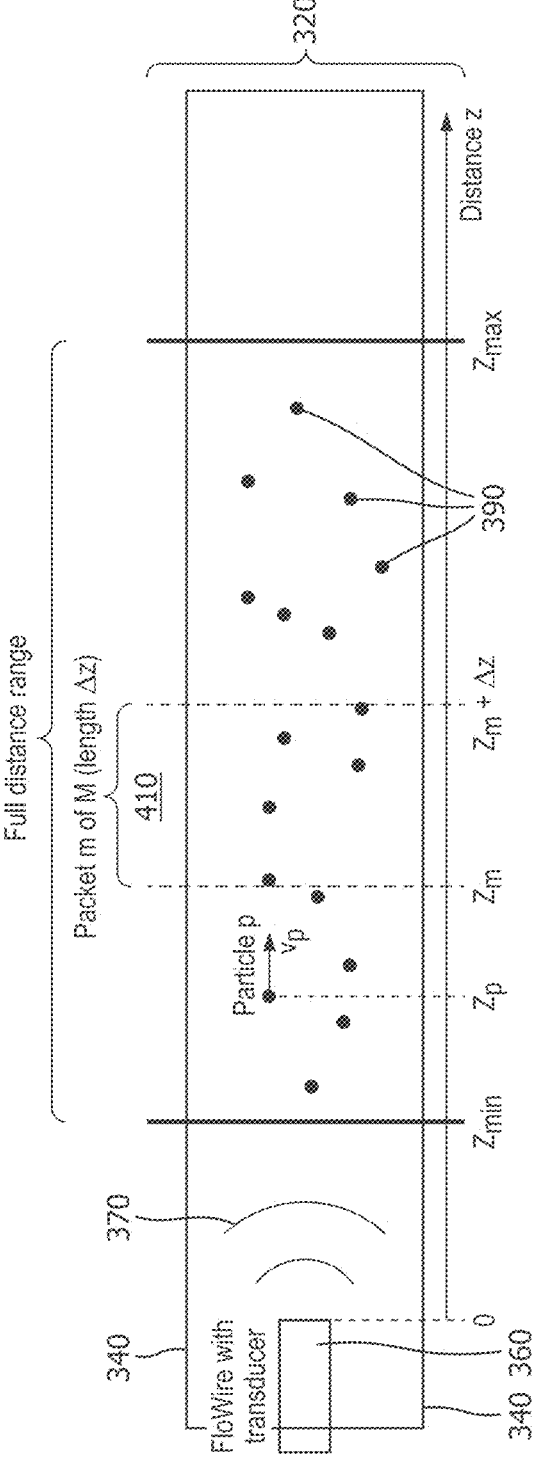
FIG. 4 is a schematic overview of a measurement of intravascular flow velocity using Doppler ultrasound, in accordance with at least one embodiment of the present disclosure.

FIG. 4 is a schematic overview of a measurement of intravascular flow velocity using Doppler ultrasound, in accordance with at least one embodiment of the present disclosure. A red blood cell velocity distribution is derived by sending an ultrasound wave or pulse 370 from the transducer 360 into the blood vessel 320. The propagating ultrasound wave or pulse 370 is backscattered by red blood cells 390. The backscattered ultrasound wave is received by the same transducer 360, which converts it into a corresponding electrical signal. In this simplified model, we only consider the axial dimension, Z. At Z=0, the transducer 360 is positioned, and creates ultrasound waves 370 that propagate in the positive Z direction. As the waves travel along the vessel, they are backscattered by cells or other particles 390 in the blood. Measurement of low velocity is performed over a distance range $[Z_{min}-Z_{max}]$ in M separate packets 410 (also known as range gates), each covering a distance range of $\Delta Z$ from a minimum range $Z_m$ to a maximum range $Z_m+\Delta Z$. All particles p have a position $Z_p$ and travel along the Z direction with a velocity $V_p$ (which is usually positive but may also be negative).

Figure 5:
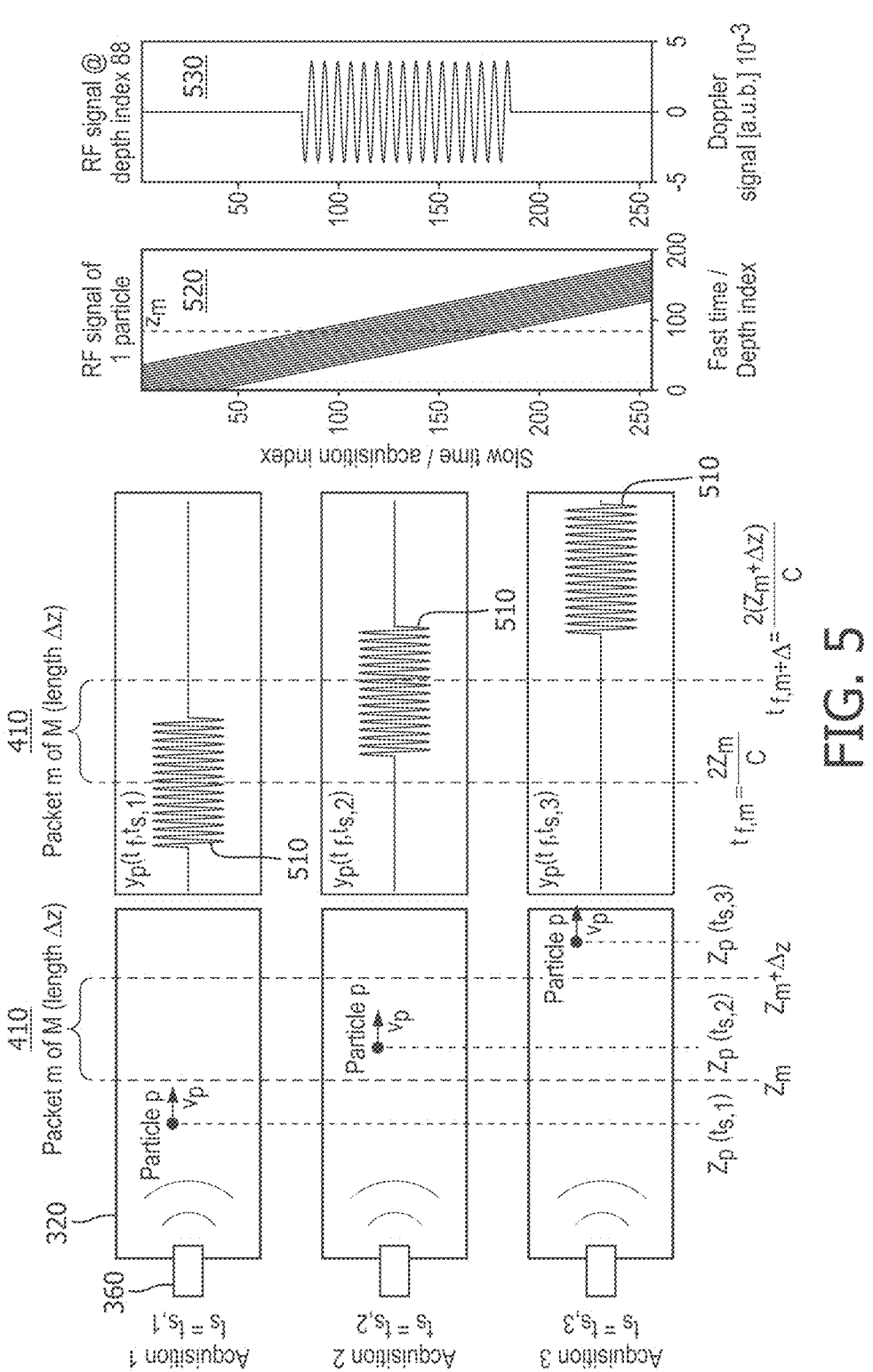
FIG. 5 is a schematic contribution of a flowing particle p within a blood vessel to the Doppler signal matrix, in accordance with at least one embodiment of the present disclosure.

FIG. 5 is a schematic contribution of a flowing particle p within a blood vessel 320 to the Doppler signal matrix, in accordance with at least one embodiment of the present disclosure. So far, this disclosure has only considered a single pulse-echo acquisition. However, in a flow-sensing modality, typically an ensemble of subsequent ultrasound pulse-echo acquisitions may be considered. The pulse-echo acquisitions may for example be repeated at a constant pulse repetition interval (PRI). In order to assess velocity, an algorithm considers the displacement of scattering particles between subsequent acquisitions, considering the effect that particles have moved in-between subsequent acquisitions as opposed to moving during a single acquisition. In other words, an algorithm may neglect the 'true' Doppler effect that would cause the frequency $f_c$ of the ultrasound wave in a single pulse-echo acquisition to change as a result of movement of the particles. Doppler analysis may be performed within so-called packets 410, which facilitates the analysis of velocity as a function of the distance Z by a suitable choice of packets with length $\Delta Z$ along the total distance range $[Z_{min}-Z_{max}]$. Graphically, this procedure is displayed in FIG. 5, which shows the pulse-echo acquisitions 510 for a single moving scattering particle as a function of slow time, whereby the slow time $t_s$ is the time covered between subsequent pulse-echo acquisitions. On the left, a particle p is shown in three successive positions as it is moving away from the transducer 360 with velocity $V_p$. In the middle, its pulse-echo contribution 510 to the received signal is shown. In the top case $(Z_p<Z_m)$, the particle is already contributing to the Doppler signal at position $Z_m$ owing to the duration of the transmitted pulse. In the middle case $(Z_m<Z_p<Z_m+\Delta Z)$, the particle has moved further but is still contributing to the Doppler signal within packet m. In the bottom case $(Z_p>Z_m+\Delta Z)$, the particle p has moved completely out of the packet 410 and is no longer contributing to the Doppler signal 520, 530. Further to the right, this particle's contribution is shown as a 2D image with the fast time $t_f$ on the horizontal axis and the slow time $t_s$ on the vertical axis. On the right, the resulting signal 530 along one particular distance/fast-time sample is displayed. The resulting signal 530 is a windowed sinusoid whose frequency (the Doppler frequency) is determined by the velocity of the particle p.

Figure 6:
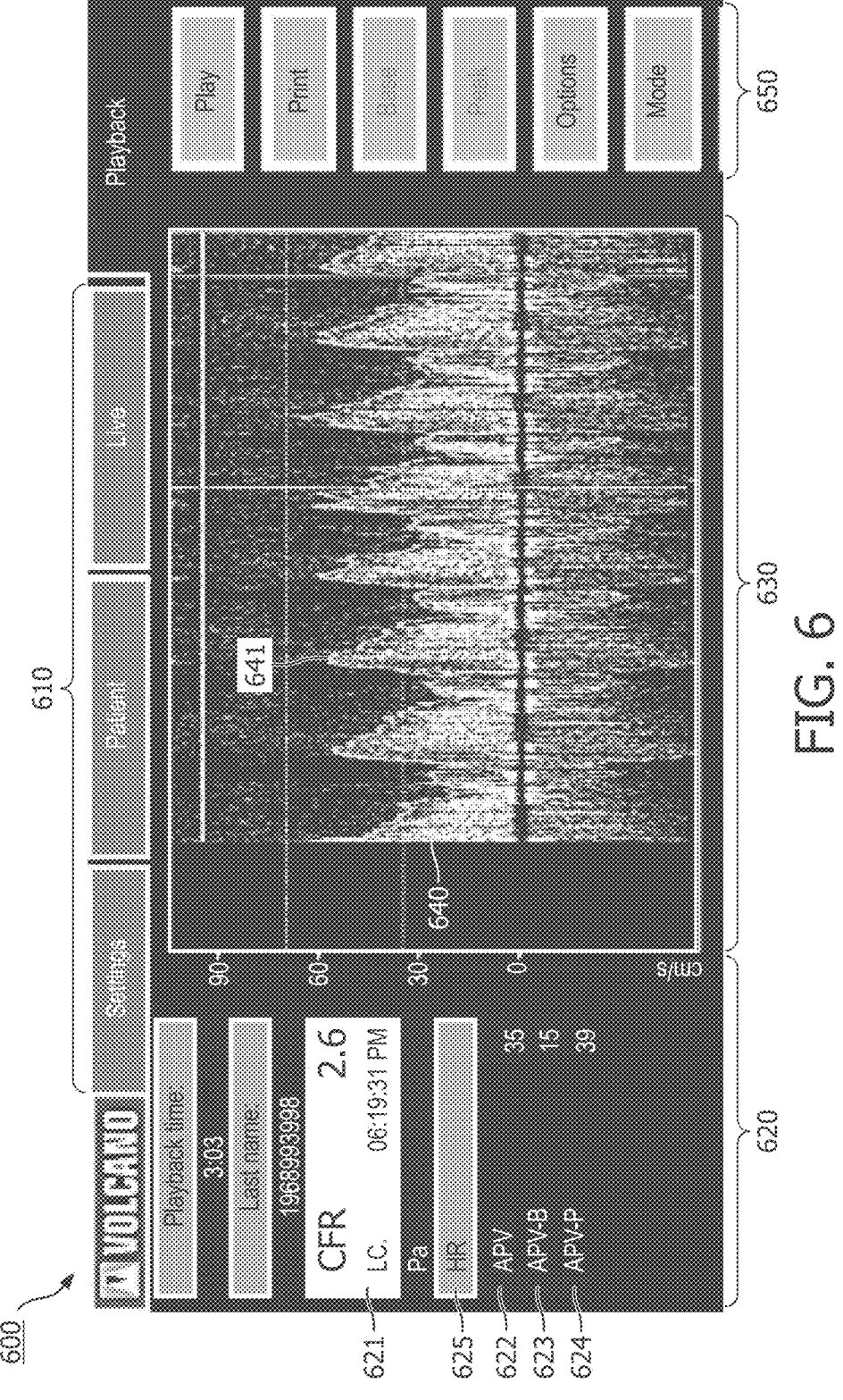
FIG. 6 is an example intravascular flow velocity measurement screen, in accordance with at least one embodiment of the present disclosure.

FIG. 6 is an example intravascular flow velocity measurement screen 600, in accordance with at least one embodiment of the present disclosure. The example intravascular flow velocity measurement screen 600 includes a control tab area 610, a control button area 650, a blood flow statistics area 620, and a waveform display area 630 that contains a waveform 640. As shown by the waveform 640, a complete red blood cell velocity distribution is acquired at regular intervals in a certain predetermined packet (volume at a certain distance from the guidewire tip). The flow velocity distribution (in the selected volume) can be graphically shown by plotting the flow velocity along the y-axis at each moment in time (x-axis), as shown by the example velocity waveform 640, and a second waveform 641 showing the instantaneous peak velocity (IPV) of the velocity waveform 640. The brightness or grey scale of the waveforms is indicative of relative incidence of a red blood cell velocity at a particular point in time.

In the example shown in FIG. 6, the blood flow statistics area 620 includes a coronary flow reserve measurement 621, an average peak velocity measurement 622, an average peak velocity baseline measurement 623, an average peak velocity hyperaemia measurement 624, and a heart rate measurement 625.

For the clinical application the maximum blood cell velocity at each point in time is determined (instantaneous peak velocity=IPV). This IPV value is averaged over a longer period of time (several cardiac cycles) to provide the average peak velocity (APV). This APV is measured during baseline (resting) conditions (APV-B) as well as during hyperaemia (APV-P). The hyperaemia condition is induced by injecting adenosine or acetylcholine into the blood. The ratio of the two provides the so-called coronary flow reserve (CFR=APV-P/APV-B). The CFR is a clinically relevant parameter. A CFR value above 2 may be clinically accepted as a healthy coronary flow reserve which does not need treatment. A value below 2 may indicate a need for intervention or follow up. The flow velocity information is shown as a grayscale waveform image 630, 640 in a display format known as a spectral Doppler visualization. The horizontal axis represents time and the vertical axis represents velocity. The grey scale is indicative of relative incidence of a particular velocity measurement at a particular point in time. In practice, as the velocity is measured over a sample volume, a distribution of velocities is measured; each vertical line in the grayscale image 630, 640 represents this distribution, measured in the form of a Doppler spectrum. The spectrum may include an instantaneous peak velocity (IPV), which indicates the maximum velocity at any point in time. This tracing can be automatically determined from the Doppler spectrum and subsequently averaged across several heart cycles to provide the average peak velocity (APV), which is numerically shown on the left-hand side in the flow statistics area 620. The APV is measured during baseline (resting) condition (APV-B) as well as during hyperaemia (in this case after intra-arterial injection of adenosine, APV-P); the ratio of the two provides the coronary flow reserve (CFR) value. In this case, the example CFR value of 2.6 above an exemplary clinically accepted threshold of 2, which may indicate a sufficiently healthy coronary flow reserve that would generally not require intervention.

One challenge of the flow measurement modality in existing systems is that the measurement result depends on the exact positioning and orientation of the transducer with respect to the vessel. This means that an expert clinician is required to position the flow wire (e.g., the ultrasound transducer at the tip of a guidewire) in order to perform a high-quality flow measurement. The quality of the flow signal can be optimized by careful manipulation of the guidewire position and orientation while visually inspecting the signal on the screen and/or by listening to the audio signal that is derived from the flow signal. The audio option is enabled by the fact that the Doppler signal (demodulated to the baseband) coincidentally happens to reside within the audible frequency range of human hearing. In clinical practice, the audio signal provides a valuable direct feedback signal for experienced users to assess the quality of the Doppler signal. This is in practice highly convenient as the user does not need to look at the screen and can fully focus on manipulation of the guidewire tip position in order to optimize the signal quality. For inexperienced users, however, the audio signal can be difficult to understand or interpret and may even be annoying. The positioning is further complicated by the fact that it needs to be done in a beating heart within moving vessels and tissue.

Figure 7:
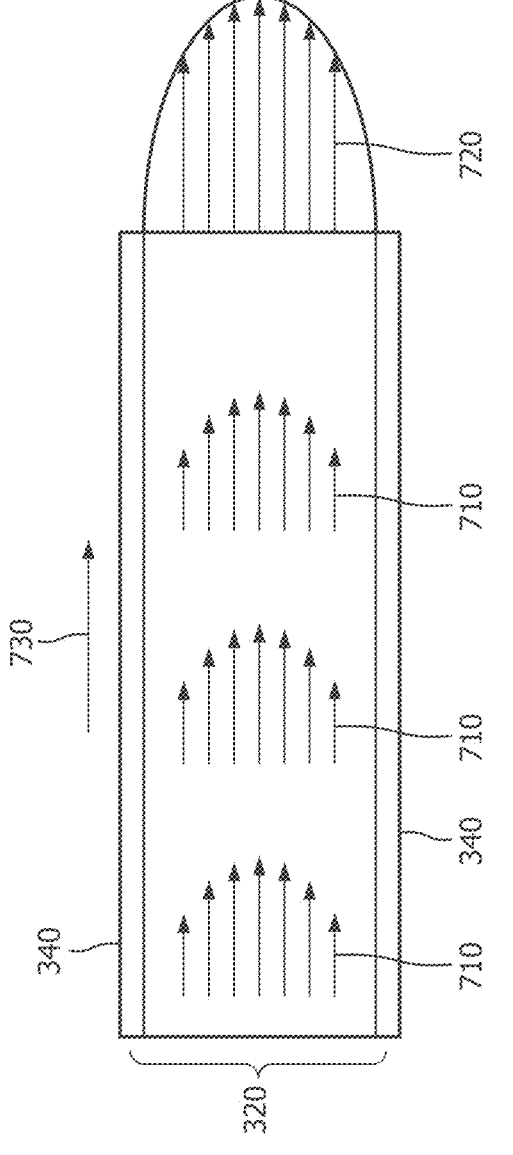
FIG. 7 is a schematic depiction of a typical laminar flow profile within a blood vessel, in accordance with at least one embodiment of the present disclosure.

FIG. 7 is a schematic depiction of a typical laminar flow profile within a blood vessel 320 with blood vessel walls 340, in accordance with at least one embodiment of the present disclosure. In an example, velocity profiles 710 taken at different distances or times may be used to compute an average or representative velocity profile 720, or an average speed or flowrate 730. In case of a straight tube and steady flow, the velocity distribution is shaped as a parabola or Poiseuille distribution.

The sensitivity of the flow measurement with respect to position and orientation of the guidewire tip has some significant challenges. For example, clinical outcomes may be dependent upon wire placement and maintaining position during blood flow velocity measurements. The measurement may thus take significantly longer than needed, resulting in additional risks for the patient and higher costs of care. As a result, there can be significant adoption barriers for clinicians to apply flow measurements in clinical practice, and thus the group of experts that can perform high-quality measurements may be fairly limited. One can identify several root causes for the undesirable measurement sensitivity. For example, the blood flow velocity is not constant throughout the cross-section of the vessel. Generally, at low velocities, the blood tends to flow without lateral mixing and exhibits a so-called laminar flow profile whereby the flow velocity is highest in the center and drops off toward the edges of the vessel. The velocity at the edge can be close to zero (e.g., a stagnant layer or boundary layer). This may for example mean that, depending on the transducer position within the cross-sectional plane of the vessel, the measured velocity profile might be different, as discussed below.

In addition, the propagation and echo of the ultrasound wave may not be limited to the blood in the vessel. The transducer beam profile may also penetrate the vessel wall and surrounding tissue. Especially in areas where the vessel is curved, the ultrasound beam may interrogate large volumes outside of the vessel. Due to cardiac movement of the tissue and vessel wall, spurious blood velocity components may be detected.

In some cases, the guidewire (and corresponding ultrasound beam) may not be well aligned with the blood flow. This means that only the axial velocity component (i.e. projected onto the central axis of the beam) is measured (cosine relation). The lateral velocity component (sine relation) is discarded or ignored by the velocity measurement. The velocity profile can also change with increasing distance from the transducer. For example, the presence of the wire can disturb the flow profile when the blood flows around it. Generally, lower velocities are observed at smaller distances from the transducer tip. However, the exact flow profile around the guidewire tip also depends on the orientation. Also, it may be that not in all areas the blood flow are laminar. For example, at bifurcations or at partial occlusions (due to calcium or plaque) the blood flow may become chaotic or turbulent.

Figures 8A, 8B, 8C, 8D:
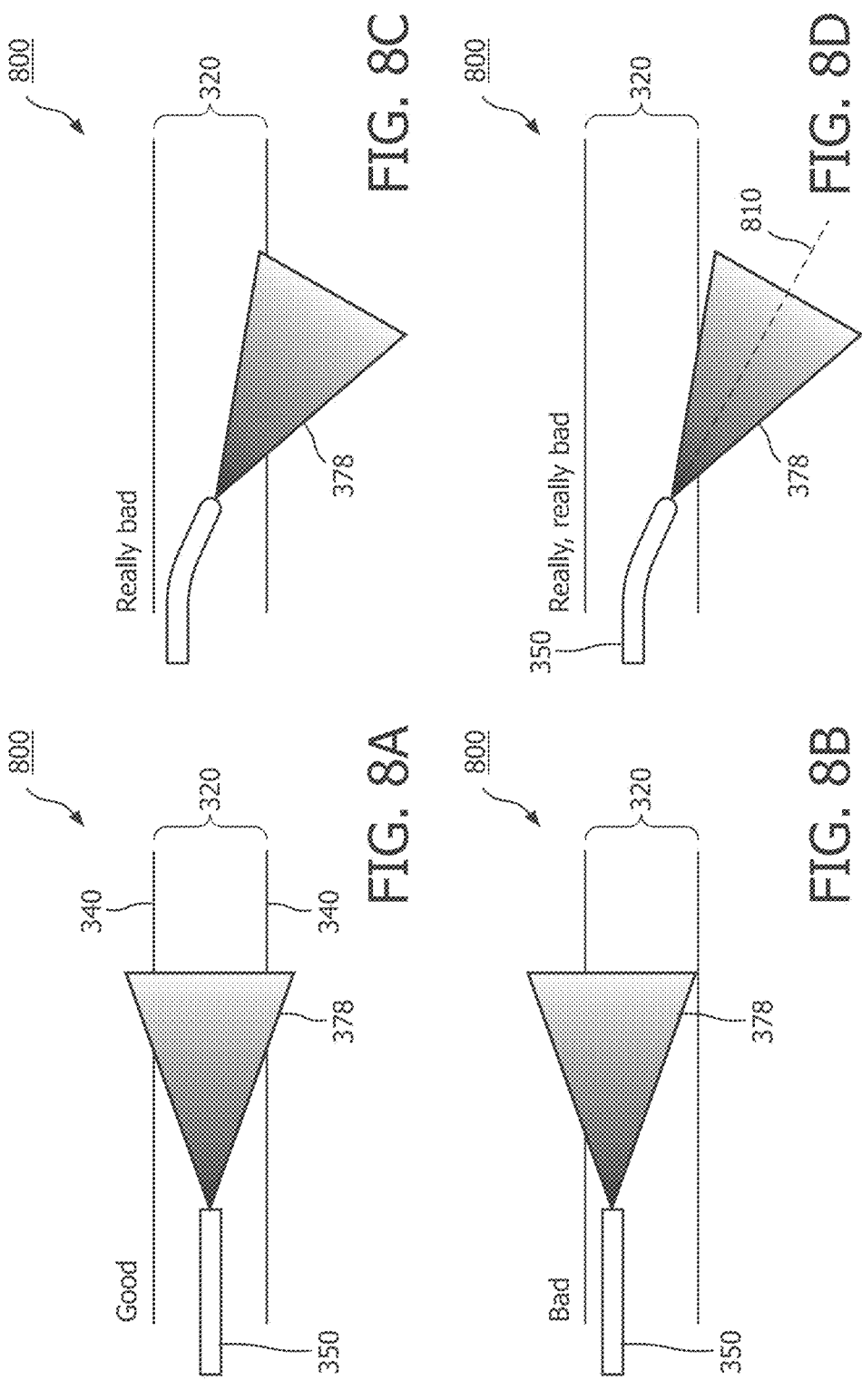
FIG. 8A is a schematic representation of guidewire position and orientation, in accordance with at least one embodiment of the present disclosure.
FIG. 8B is a schematic representation of guidewire position and orientation, in accordance with at least one embodiment of the present disclosure.
FIG. 8C is a schematic representation of guidewire position and orientation, in accordance with at least one embodiment of the present disclosure.
FIG. 8D is a schematic representation of guidewire position and orientation, in accordance with at least one embodiment of the present disclosure.

FIG. 8A is a schematic representation 800 of guidewire position and orientation, in accordance with at least one embodiment of the present disclosure. In an ideal case, the guidewire 350 is straight, and is aligned with and positioned midway between the walls 340 of the blood vessel 320, such that the viewing cone 378 (e.g., a centerline of the viewing cone) is parallel with the blood vessel 320 and impinges minimally and symmetrically on the vessel walls 340, such that echoes from the vessel walls 340 do not play a major role in the ultrasound echoes returning to the transducer.

FIG. 8B is a schematic representation 800 of guidewire position and orientation, in accordance with at least one embodiment of the present disclosure. In a less ideal case, the guidewire 350 is straight, and is aligned with the walls 340 of the blood vessel 320, but is positioned significantly closer to one wall 340 than to the opposite wall. In such cases, the viewing cone 378 may be parallel with the blood vessel 320, but impinges significantly on one of the vessel walls 340, such that echoes from the vessel wall 340 play a more significant role in the ultrasound echoes returning to the transducer.

FIG. 8C is a schematic representation 800 of guidewire position and orientation, in accordance with at least one embodiment of the present disclosure. In an even less ideal case, the guidewire 350 is bent, and is aligned at least partially toward a wall 340 of the blood vessel 320, but is positioned with the tip of the guidewire close to a centerline of the vessel. In such cases, the viewing cone 378 may be angled with respect to blood flow within the vessel 320, such that the measured blood velocity is reduced (e.g., by a cosine factor of the angle to the blood flow). In addition, the viewing cone 378 impinges significantly on the vessel wall 340, such that echoes from the vessel wall 340 play a significant role in the ultrasound echoes returning to the transducer.

FIG. 8D is a schematic representation 800 of guidewire position and orientation, in accordance with at least one embodiment of the present disclosure. In a poor measurement case, the guidewire 350 is bent, and is aligned at least partially toward a wall 340 of the blood vessel 320, and is positioned significantly closer to that wall 340 than to the opposite wall. In such cases, the viewing cone 378 may be angled with respect to blood flow within the vessel 320, such that the measured blood velocity is reduced (e.g., by a cosine factor of the angle to the blood flow), and is also reduced by the boundary layer effect that causes blood to flow more slowly near the walls of a vessel than near the center. In addition, the viewing cone 378 occurs almost entirely within the vessel wall 340, such that echoes from the vessel wall 340 play a dominant role in the ultrasound echoes returning to the transducer.

For reference, the longitudinal direction (e.g., the centerline of the viewing cone 378) is shown.

The above variety of root-causes makes it difficult for the clinical user to identify clear rules on guidewire positioning. A good quality flow measurement depends generally on craftsmanship and extensive experience of the clinician. It is an object of the present disclosure to overcome the aforementioned drawbacks and to lower the barrier for adoption of the flow modality in assessing CVD, NO-CAD, MVD, and other vascular health issues, thereby enabling significant growth of the market share for flow-based assessments compared to competing technologies, such as thermosdilution.

Figure 9:
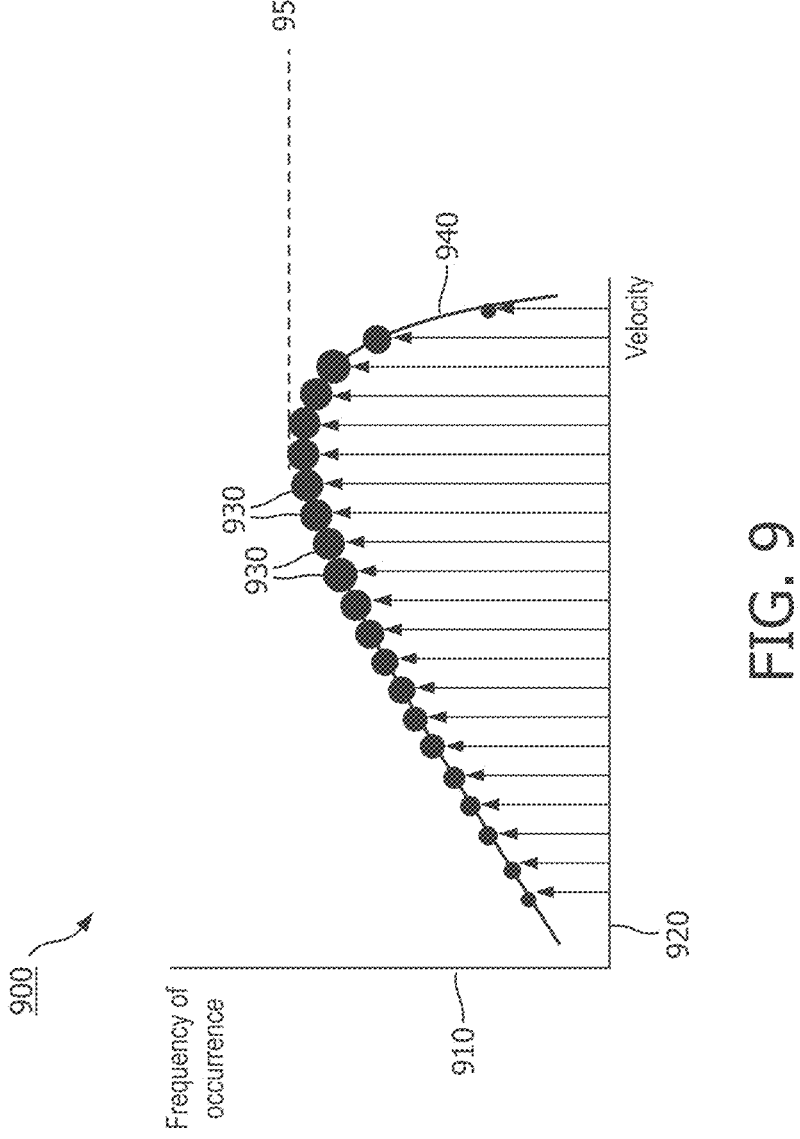
FIG. 9 is a velocity histogram of a Doppler spectrum representing blood flow within a vessel, in accordance with at least one embodiment of the present disclosure.

FIG. 9 is a velocity histogram 900 of a Doppler spectrum or velocity spectrum representing blood flow within a vessel, in accordance with at least one embodiment of the present disclosure. The samples are taken throughout the cardiac cycle and displayed graphically, such that each circle 930 represents the number if instances of the corresponding velocity in the sample volume.

After the Doppler signal is transformed into the frequency domain (e.g., though a fast Fourier transform or FFT), it is displayed as a vertical histogram of frequency of occurrence 910 vs. velocity 920. Higher frequencies of occurrence are represented by larger circles 930, whereas lower frequencies of occurrence are represented by smaller circles 930. E.g., in this example, the height of the circles conveys the same information as the size of the circles. Other means of displaying a velocity spectrum may be used instead or in addition.

In case of a straight tube and steady flow the velocity distribution is shaped as a parabola (Poiseuille distribution, see FIG. 7). However, in the case of good transducer alignment, most of the velocities that are measured will be in the high range, resulting in a velocity histogram which is skewed to the high velocities, such that the histogram curve 940 shows an asymmetric peak 950 that is peak-shifted to the right, e.g., toward higher velocities.

For each velocity histogram, the index algorithm calculates a value indicative of the quality of the signal. An optimal signal is defined as a Doppler Spectrum with velocities predominantly near the highest velocity in the spectrum referred to as instantaneous peak velocity (IPV). Having the highest frequency of occurrence at velocities in the spectrum near the IPV is a strong indication the transducer is aligned with the axis of the vessel and, if the transducer is pointing down the center of the vessel, measurements will generally show a majority of the velocity spectrum near the IPV. An additional benefit of having a majority of the velocity spectrum skewed towards the maximum is an increase in the signal to noise ratio (SNR). This provides the IPV detection algorithm a better opportunity to discriminate between background scatter (e.g., noise) and signal.

A Doppler derived parameter can aid in the optimal positioning of the Doppler Guide Wire (DGW) within the vessel lumen. In an example, the derived parameter utilizes the time-averaged, spectral-peak velocity (APV) and the normalized first Doppler moment (M1/M0) to develop a DGW position indicator. Optimal positioning of the DGW was identified at the position where maximum APV and M1/M0 were obtained.

$$0^{th} \text{ Moment} = P = \int_{V_1}^{V_2} S(v)dv \qquad \text{EQN 1}$$

$$1^{st} \text{ Moment} = \langle v \rangle = \frac{\int_{v_1}^{v_2} vS(v)dv}{P} \qquad \text{EQN 2}$$

In this case, the first Doppler moment is normalized to a unit area by dividing by the zeroth Doppler moment to get the mean velocity. However, this process does not assess the overall shape of the velocity spectrum, and is dependent on many physiological variables and thus requires significant interpretation by clinicians.

More desirable is an index that assesses the degree of skewness of the velocity spectrum towards the IPV, and that is also independent of the amplitude and width of the spectrum. The following is one example of an algorithm that satisfies the goals of an index by discriminating between velocity spectra skewness towards the IPV. By multiplying the frequency of occurrence (FO) by the velocity (VEL), velocity profiles that are skewed towards the IPV will have a higher value than velocity profiles skewed toward zero velocity.

$$\text{Index}_1 = \sum (FO_n \times VEL_n) \qquad \text{EQN 3}$$

Unfortunately, the above equation is susceptible to the variations in velocity magnitude during the cardiac cycle. Ideally, the index needs to assign a similar value to similarly skewed velocity profiles, regardless of width or amplitude.

Figures 10A, 10B:
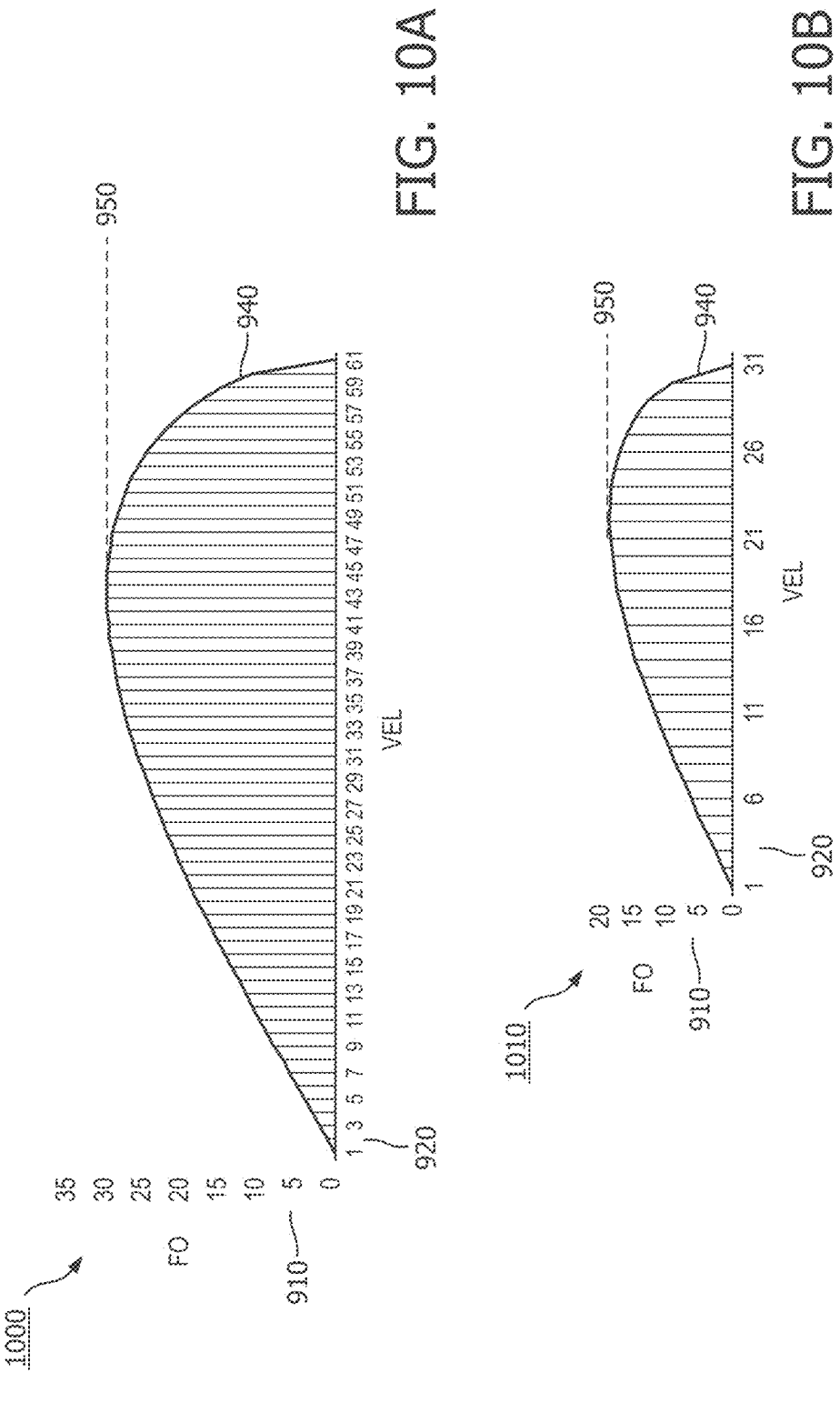
FIG. 10A is a graph showing a high velocity, high frequency of occurrence velocity spectrum that is peak-shifted to the right, in accordance with at least one embodiment of the present disclosure.
FIG. 10B is a graph showing a low velocity, low frequency of occurrence, velocity spectrum that is peak-shifted to the right, in accordance with at least one embodiment of the present disclosure.

FIG. 10A is a graph 1000 showing a high velocity, high frequency of occurrence velocity spectrum that is peak-shifted to the right, e.g., towards the IPV, in accordance with at least one embodiment of the present disclosure. In case of good alignment, most of the velocities that are measured will be in the high range, resulting in a velocity histogram which is skewed to the high velocities. As can be seen, the curve 940 representing frequency of occurrence 910 vs. velocity 920 has a peak 950 that is shifted toward the right (e.g., toward higher velocities), such that the curve 940 is asymmetric.

FIG. 10B is a graph 1010 showing a low velocity, low frequency of occurrence, velocity spectrum that is peak-shifted to the right, e.g., towards IPV, in accordance with at least one embodiment of the present disclosure. As with FIG. 10A, FIG. 10B shows good alignment of the Doppler transducer, as shown by the peak 950 shifted toward the right (e.g., to higher velocities). However, in this case, the greatest frequency of occurrence is only 15 per measurement period (a dimensionless representation that may indicate a number of samples, a signal energy, or a fraction of signal energy), vs. 30 per measurement period for FIG. 10A, and the greatest velocity is 31 centimeters per second, vs. 61 cm/s for FIG. 10A. However, despite the different amplitude and width of the spectra shown in FIGS. 10A and 10B, it is desirable for a quality index, skew index, skewness parameter, or spectral flow assessment index to yield similar values for both curves, since they have similar shapes, both indicating good transducer alignment.

To account for differences in FO and VEL, each parameter can be normalized to its respective scale. Here we calculate the ratio of mean velocity divided by the maximum velocity. This is our new skewness index. This ratio may for example be between 0 and 1 (exclusive). A value of 0.5 represents a symmetric profile (as shown for example in FIG. 11B), while a value between 0.5 and 1 represents a peak shift to the right (as shown for example in FIGS. 11A and 12), and a value between 0 and 0.5 represents a peak shift to the left (as shown for example in FIGS. 11C and 14). Since we prefer a peak shift to the right, higher values of the skew index are preferred. Note that is a discrete implementation of the 1st central moment (e.g., EQN 2) which in effect calculates the mean velocity. Thus:

$$\text{Index}_1 = \frac{\sum FO_n \cdot VEL_n}{\sum FO_n} \qquad \text{EQN 4}$$

$$\text{Index}_2 = \frac{\text{Index1}}{\text{Max}_{VEL}} \qquad \text{EQN 5}$$

Where $\text{Max}_{VEL}$ is the maximum velocity for the entire velocity profile, (e.g., the IPV).

In some embodiments, to account for the relative differences in scales, the previously normalized values may then be normalized by the relative scale maximums:

Example indices obtained using representative velocity profiles are as follows:

TABLE 1

| Computed skew indices for different waveforms | | | | | |
|---|---|---|---|---|---|
| Short skew peak shift to the right (FIG. 11A) | Long skew peak shift to the right (FIG. 12) | Short no skew (FIG. 11B) | Long no skew (FIG. 13) | Short skew peak shift to the left (FIG. 11C) | Long skew peak shift to the left (FIG. 11) |
| 0.59 | 0.59 | 0.5 | 0.5 | 0.41 | 0.41 |

These features make the skew index useful for determining, with a single dimensionless value, the shape of the velocity spectrum, with higher index values showing a peak shift to the right, thus indicating favorable alignment of the transducer. Depending on the implementation, other equations may be used to compute the quality index, skew index, or spectral flow assessment index from the velocity spectrum or from the raw velocity measurements, and that the index may be dimensional or non-dimensional. Such embodiments expressly fall within the scope of the present disclosure. For example, other features that could be used as skewness index include but are not limited to:

Pearson's moment coefficient of skewness=$E[((x-mu)/sigma)^3]$

Pearson's first skewness coefficient: (mean−mode)/standard deviation

Pearson's second skewness coefficient 3*(mean−median)/standard deviation

Nonparametric skew (mean−median)/standard deviation

Bowley's coefficient of skewness (based on quartiles)

Ratio of median or mode with respect to IPV

Ratio of median divided by mean

Figure 11A:
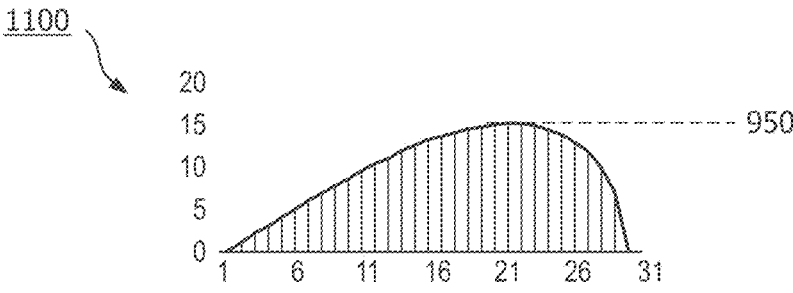
FIG. 11A is a graph showing a low velocity, low frequency of occurrence velocity spectrum that is peak-shifted to the right, in accordance with at least one embodiment of the present disclosure.

FIG. 11A is a graph 1100 showing a low velocity, low frequency of occurrence velocity spectrum that is peak-shifted toward the right (e.g., towards the IPV), in accordance with at least one embodiment of the present disclosure. In statistical/stochastic terminology, this would be called 'left skew' or 'negative skew' since the tail of the distribution is to the left. As with FIG. 10B, this graph shows good alignment of the Doppler transducer, as shown by the peak 950 shifted toward the right (e.g., to higher velocities). This skew will generally result in the highest values for the skew index, and a threshold may be selected for the index to detect whether the transducer is properly aligned. Possible threshold values may be 0.5, 0.55 or 0.6. Generally, higher values may be preferred. However, higher threshold levels may be more restrictive or more difficult to reach, as evidenced by Table 1, where values remain relatively close to 0.5

Figure 11B:
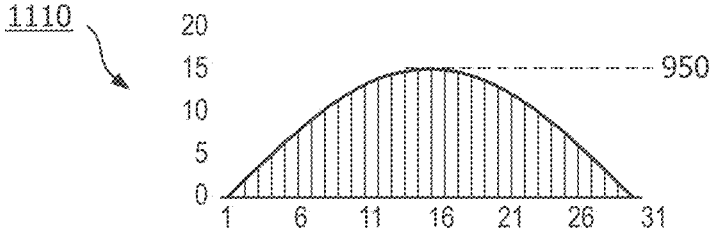
FIG. 11B is a graph showing a low velocity, low frequency of occurrence velocity spectrum that is approximately symmetric, in accordance with at least one embodiment of the present disclosure.

FIG. 11B is a graph 1110 showing a low velocity, low frequency of occurrence velocity spectrum that is approximately symmetric (e.g., no skew), in accordance with at least one embodiment of the present disclosure. This graph shows moderately poor alignment of the Doppler transducer, as shown by the peak 950 being centrally and symmetrically located (e.g., no skew toward higher velocities). This may indicate either moderately poor orientation (e.g., away from the vessel centerline) or moderately poor placement (again, away from the vessel centerline) of the Doppler transducer.

Figure 11C:
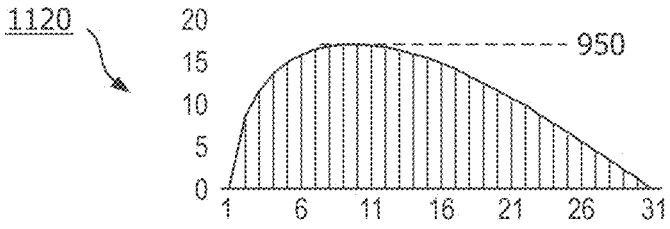
FIG. 11C is a graph showing a low velocity, low frequency of occurrence velocity spectrum that is peak-shifted to the left, in accordance with at least one embodiment of the present disclosure.

FIG. 11C is a graph 1120 showing a low velocity, low frequency of occurrence, velocity spectrum that is peak-shifted to the left (e.g., toward lower velocities, and thus 'skewed right' in statistical parlance, in some embodiments), in accordance with at least one embodiment of the present disclosure. This graph shows poor alignment of the Doppler transducer, as shown by the peak 950 shifted toward the left (e.g., to lower velocities), indicating that the transducer is either pointed away from the vessel centerline, or is too close to the vessel wall, or both.

Figure 12:
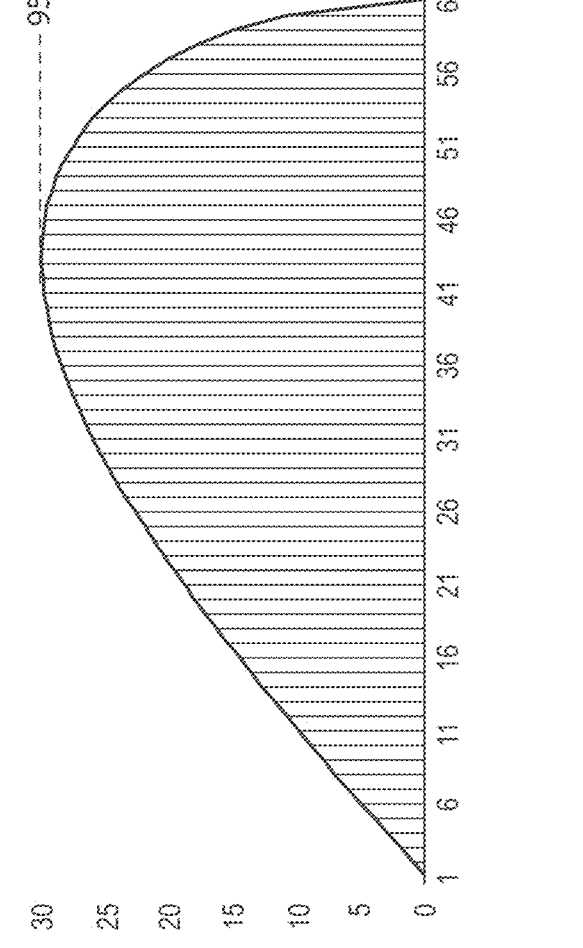
FIG. 12 is a graph showing a high velocity, high frequency of occurrence velocity spectrum that is peak-shifted to the right, in accordance with at least one embodiment of the present disclosure.

FIG. 12 is a graph 1200 showing a high velocity, high frequency of occurrence velocity spectrum that is peak-shifted to the right, e.g., towards the IPV (e.g., toward higher velocities), in accordance with at least one embodiment of the present disclosure. As with FIG. 10A this graph shows good alignment of the Doppler transducer, as shown by the peak 950 shifted toward the right (e.g., to higher velocities). This skew will generally result in the highest values for the skew index, and a threshold may be selected for the index (e.g., values above 0.5) to detect whether the transducer is properly aligned.

Figure 13:
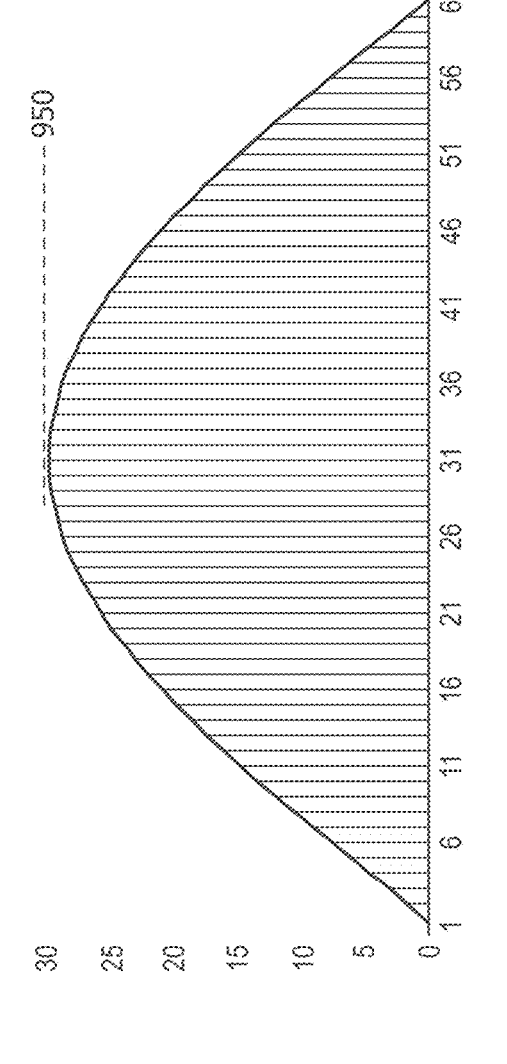
FIG. 13 is a graph showing a high velocity, high frequency of occurrence velocity spectrum that is approximately symmetric, in accordance with at least one embodiment of the present disclosure.

FIG. 13 is a graph 1300 showing a high velocity, high frequency of occurrence velocity spectrum that is approximately symmetric (e.g., no skew), in accordance with at least one embodiment of the present disclosure. This graph shows moderately poor alignment of the Doppler transducer, as shown by the peak 950 being centrally and symmetrically located (e.g., no skew toward higher velocities). This may indicate either moderately poor orientation (e.g., away from the vessel centerline) or moderately poor placement (again, away from the vessel centerline) of the Doppler transducer.

Figure 14:
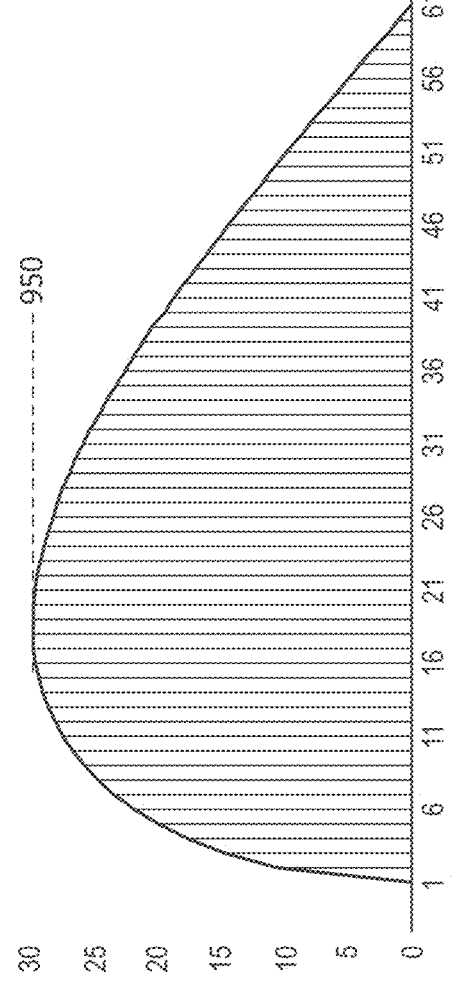
FIG. 14 is a graph showing a high velocity, high frequency of occurrence, velocity spectrum that is peak-shifted to the left, in accordance with at least one embodiment of the present disclosure.

FIG. 14 is a graph 1400 showing a high velocity, high frequency of occurrence, velocity spectrum that is peak-shifted to the left (e.g., toward lower velocities, and thus 'skewed right' in statistical parlance, in some embodiments), in accordance with at least one embodiment of the present disclosure. This graph shows poor alignment of the Doppler transducer, as shown by the peak 950 shifted toward the left (e.g., to lower velocities), indicating that the transducer is either pointed away from the vessel centerline, or is too close to the vessel wall, or both.

Figure 15:
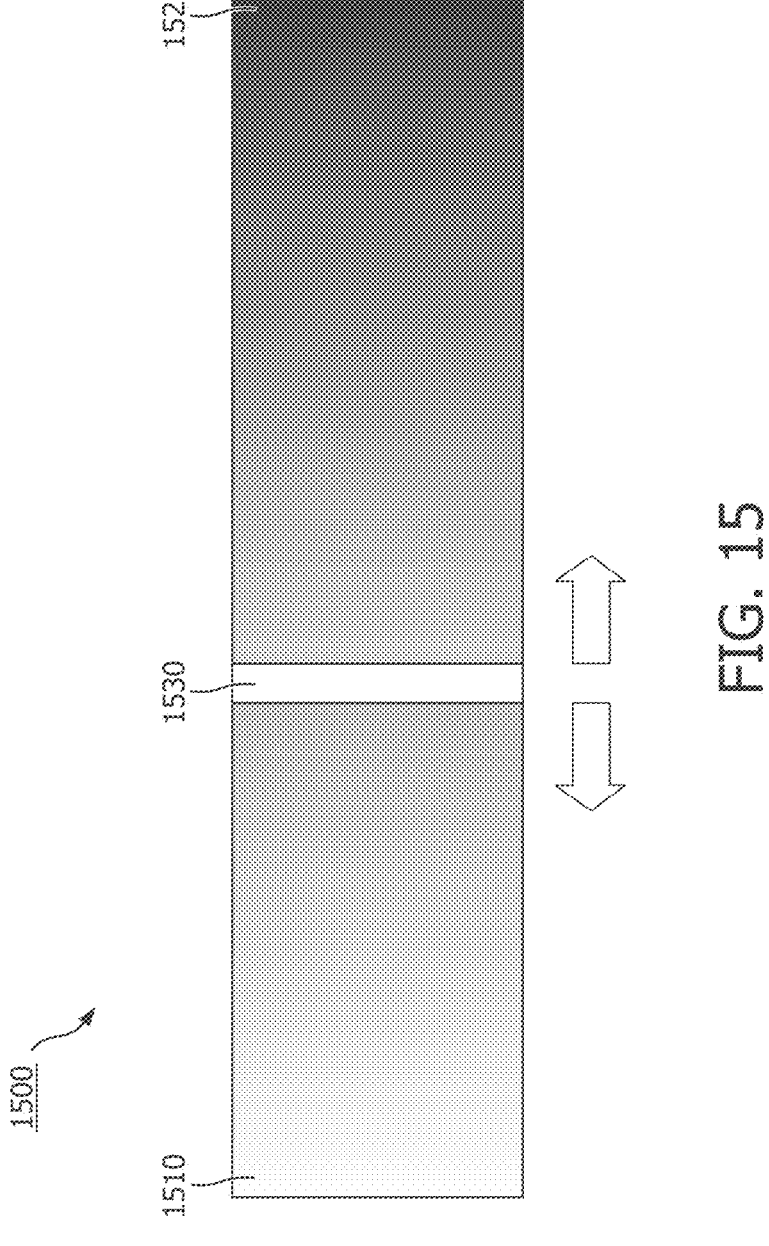
FIG. 15 shows a user interface feature or linear indicator that can be added to a user interface to provide guidance on guidewire positioning and orientation, in accordance with at least one embodiment of the present disclosure.

FIG. 15 shows a user interface feature or linear indicator 1500 that can be added to a user interface to provide guidance on guidewire positioning and orientation, in accordance with at least one embodiment of the present disclosure. The skew index, quality index, or spectral flow assessment index may be deployed or applied in several ways. In a non-limiting example, it may be a numerical value indicating the optimal position of the wire, or a dynamic graphical control, e.g., length of bar, color code indicating the optimal wire position. Instead or in addition, it may be incorporated into the feedback loop of a device that automatically controls the wire tip angle or position. The algorithm may be detected by observation, either by viewing the screen for some type of visual feedback or observing the change in signal strength without user intervention.

In the example shown in FIG. 15, the linear indicator 1500 includes a high-quality side 1510 (which may for example be colored green or white) and a low-quality side 1520 (which may for example be colored red or black), and a sliding marker 1530 that may move left and right in response to changing values of the skew index, indicating improvement or worsening of the guidewire positioning for accurate flow measurement as the clinician rotates or otherwise moves the guidewire. In an example, the clinician may not want to record measurements unless the indicator 1500 is more than halfway, or more than three quarter of the way, toward the high-quality side 1510, indicating values of the skew index that exceed a threshold value and are thus indicative of a right skew (e.g., a skew toward the instantaneous peak velocity), and thus of proper placement of the Doppler sensor at the tip of the guidewire.

Other types of indicators, based on the value of the skew index, may be used instead or in addition, including colors (e.g., red for poor alignment, yellow for moderate alignment, and green for good alignment), numerical values, analog gauges, pie charts, bar charts, audio tones, visual elements that change size or shape in response to changes in the skew index, or textual or verbal warnings or instructions to the clinician. In other embodiments, an audible tone or indicator, different from the Doppler chirp and indicative of the skew index, may be generated.

Figure 16:
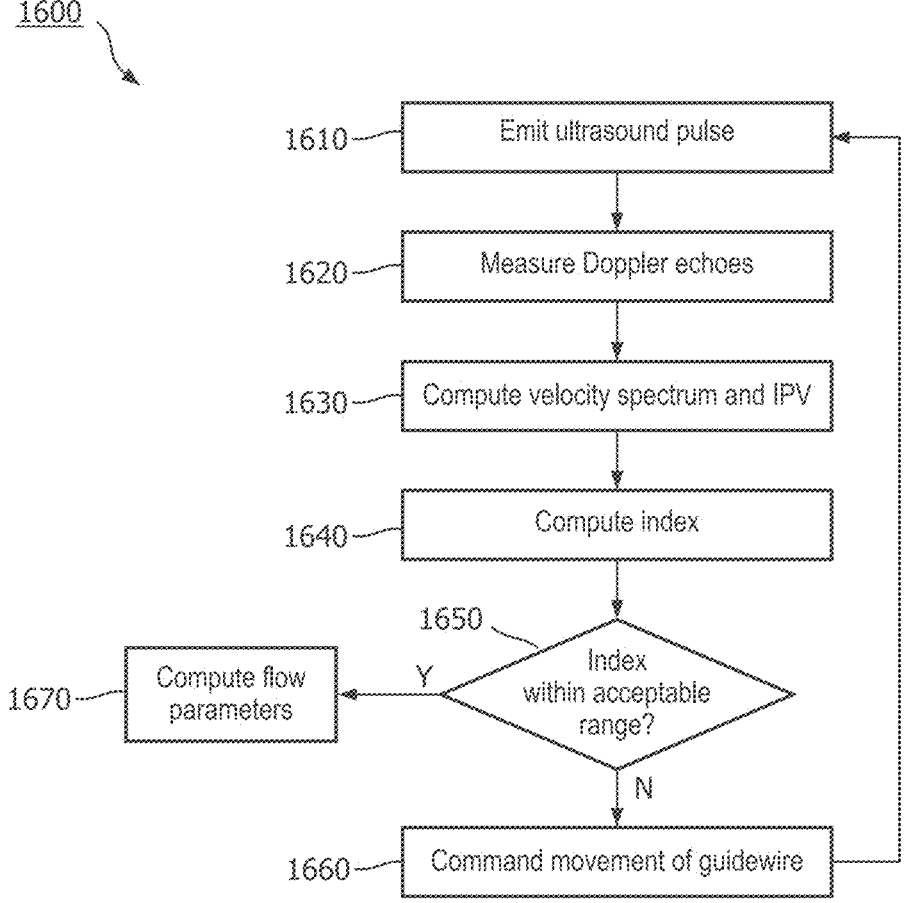
FIG. 16 shows a flow diagram of an example velocity spectrum skew determination method, according to at least one embodiment of the present disclosure.

FIG. 16 shows a flow diagram of an example velocity spectrum skew determination method 1600 according to at least one embodiment of the present disclosure. It is understood that the steps of method 1600 may be performed in a different order than shown in FIG. 16, additional steps can be provided before, during, and after the steps, and/or some of the steps described can be replaced or eliminated in other embodiments. One or more of steps of the method 1600 can be carried by one or more devices and/or systems described herein, such as processing system 306 or Patient Interface Monitor 304 of FIG. 1 and/or processor circuit 2150 of FIG. 21, or other components of the intravascular sensing system 100.

In step 1610, the method 1600 includes emitting an ultrasound pulse from the Doppler transducer at the tip of the guidewire.

In step 1620 the method includes measuring the echoes that return to the transducer from the pulse, and computing the Doppler shift for each echo, such that each returning echo represents the velocity of a particle (e.g., blood cell) moving through the body lumen (e.g., a blood vessel).

In step 1630, the method includes computing the velocity spectrum and instantaneous peak velocity (IPV). This may involve, for example, identifying which samples are suspected to be noise and which samples are suspected to be genuine velocity measurements. Such identification may for example involve a Fourier transform or other transform to pre-process the spectrum prior to skewness calculation, and can be performed on power spectra, magnitude spectra, or on a log scale. The removal may involve subtraction of noise level, removal of spectral components not related to blood flow velocity (e.g., wall motion), possible replacement of removed spectral components by model fitting using (e.g. a polynomial model), model fitting (e.g. fit the entire spectrum by, e.g., a polynomial model). The method then includes computing a histogram using only the genuine measurements or fitted models.

In step 1640, the method includes calculating a dimensional or non-dimensional quality index, skew index, or spectral flow assessment index from the computed velocity spectrum and IPV, as described above.

In step 1650, the method includes evaluating the calculated index to determine whether it falls within an acceptable range. In a non-limiting example, values higher than 0.5 may be considered indicative of good transducer alignment, whereas values equal to or less than 0.5 may be considered indicative of poor transducer alignment. If the index falls within an acceptable range, execution proceeds to step 1670. If not, execution proceeds to step 1660.

In step 1660, the method includes commanding a movement (e.g., rotation or translation) of the guidewire in order to change the position and/or alignment of the transducer. The movement may for example be a small rotation (e.g., 15 degrees or 30 degrees, although other values both larger or smaller may be used instead or in addition) or a small translation (e.g., one millimeter forward or backward, although other values could be used). Execution then returns to step 1610.

In step 1670, the method includes accepting the flow spectrum as a reliable measurement of flow velocities within the lumen, and calculating one or more flow parameters such as Coronary Flow Reserve (CFR), Microvascular Resistance Index (MRI), Hyperemic Microvascular Resistance (HMR), or Index of Microcirculatory Resistance (IMR) based on the flow spectrum and a pressure measurement. Other parameters may be calculated instead or in addition. In some embodiments, one or more indices are computed continuously (e.g., at step 1630) regardless of the skew index value. In such embodiments, step 1670 may include displaying the computed indices. In some embodiments, indices may be computed and displayed continuously, in which case step 1670 may include providing an indication (whether visual or otherwise) that the indices may be considered valid. For example, the displayed indices may switch from being displayed in a red color to being displayed in a green color.

Figure 17:
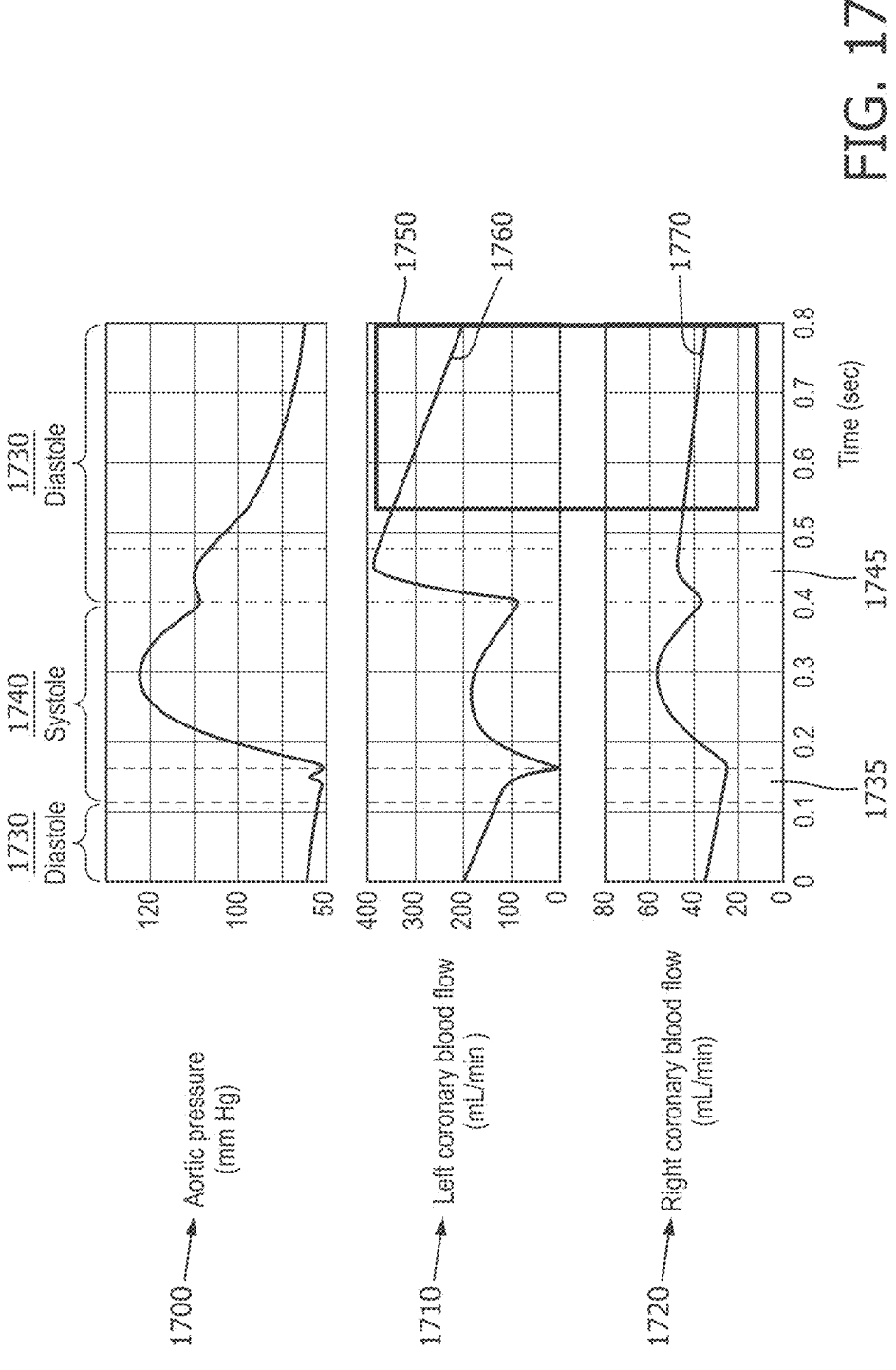
FIG. 17 is a graphical representation of aortic pressure, left coronary blood flow, and right coronary blood flow, in accordance with at least one embodiment of the present disclosure.

FIG. 17 is a graphical representation of aortic pressure 1700, left coronary blood flow 1710, and right coronary blood flow 1720, in accordance with at least one embodiment of the present disclosure. The representation includes two partial diastole periods 1730 and a systole period 1740, as well as transition periods 1735 and 1745. The flow in the coronary arteries is not steady but varies with the cardiac cycle (e.g., as an interplay between the aortic pressure and the coronary microvascular impedance). FIG. 17 shows the effect of this interplay on the flowrates 1760 and 1770 of the left and right coronary arteries. This shows the acceleration and deceleration of the blood, hence a steady flow assumption may not hold true. Considering the dimensionless Womersley number in coronary arteries of about 2-4, the velocity distribution in the vessel may also not remain a parabola during the acceleration and deceleration as the fluid. The best period to determine the skewness quality parameter for coronary arteries may be in diastole, after the large acceleration has taken place, and/or in a wave-free period (similar to iFR). Determination of the diastole period can be based on various physiological signals, e.g. ECG, pressure measurement, or the flow signal itself.

Thus, a measurement window 1750 can be determined, wherein the left and right coronary blood flow measurements 1760 and 1770 decline in a steady, approximately linear fashion. In some embodiments, the measurement window 1750 may be a particularly favorably time to collect velocity spectra from which a reliable skew index can be computed.

In some embodiments, skewness parameters measured across the measurement window 1750 are expected to be similar, allowing for temporal smoothing to increase robustness of the index as an indicator of transducer alignment. Large variations in skewness over the course of the diastole period may be an indication of bad signal quality and thus of poor transducer positioning and/or poor transducer alignment.

Figure 18:
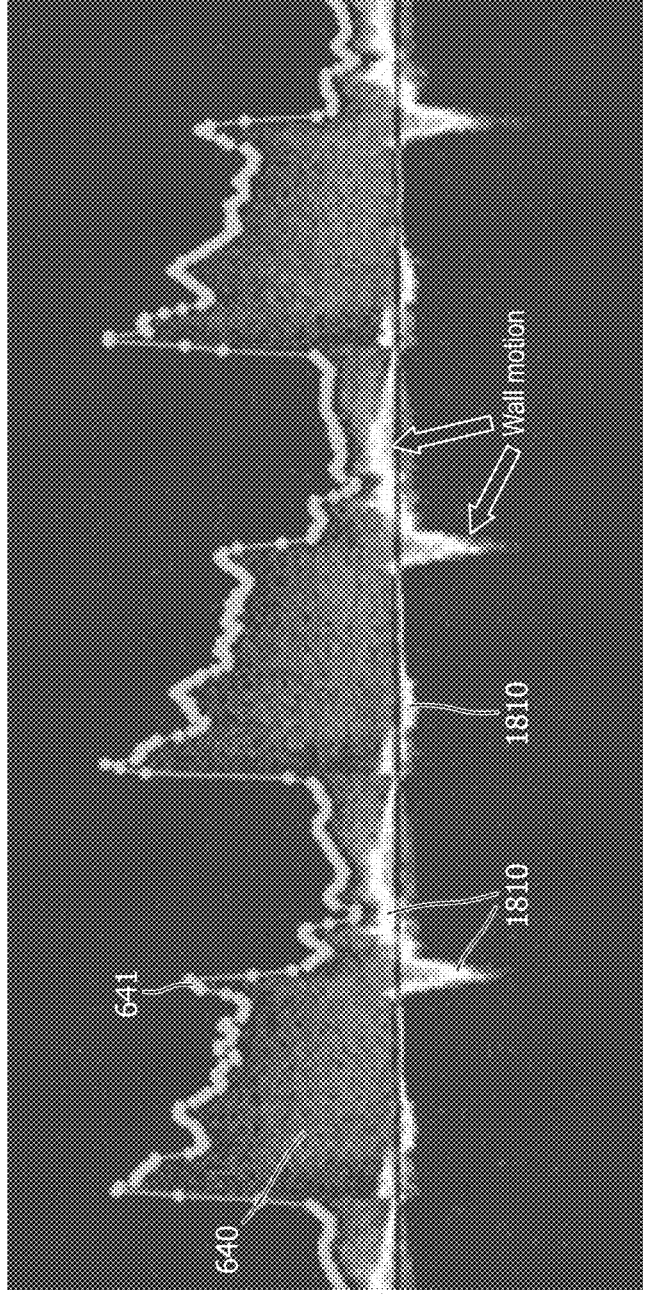
FIG. 18 is a graphical representation of a velocity-vs-time waveform and an instantaneous peak velocity curve, in accordance with at least one embodiment of the present disclosure.

FIG. 18 is a graphical representation 1800 of a velocity-vs-time waveform 640 and an instantaneous peak velocity (IPV) curve 641, in accordance with at least one embodiment of the present disclosure. The waveform 640 includes multiple velocity measurements at each time, with the y-value indicating velocity and the brightness indicating the number of particles detected at that velocity. The waveform 640 shows a clear, strong signal 1810 around the lower velocities, which can be indicative of wall motion. If included, velocity measurements from wall motion can affect the skew index computed from the velocity spectrum by creating a spike near the lower frequencies. As the wall velocities are not relevant for the detection of the maximum velocity, they can be ignored in the quality indicator, such that the skew index is determined only from velocities other than wall motion. This can be done for example by discarding all velocity measurements below a certain threshold velocity (such as, for example, 5 centimeters per second, although other values both larger and smaller may be used instead or in addition), or through a pattern recognition algorithm (e.g., a machine learning or other artificial intelligence algorithm) trained or designed to identify and exclude wall motion detections while including other low velocity measurements that are determined to be from genuine flow.

Figure 19:
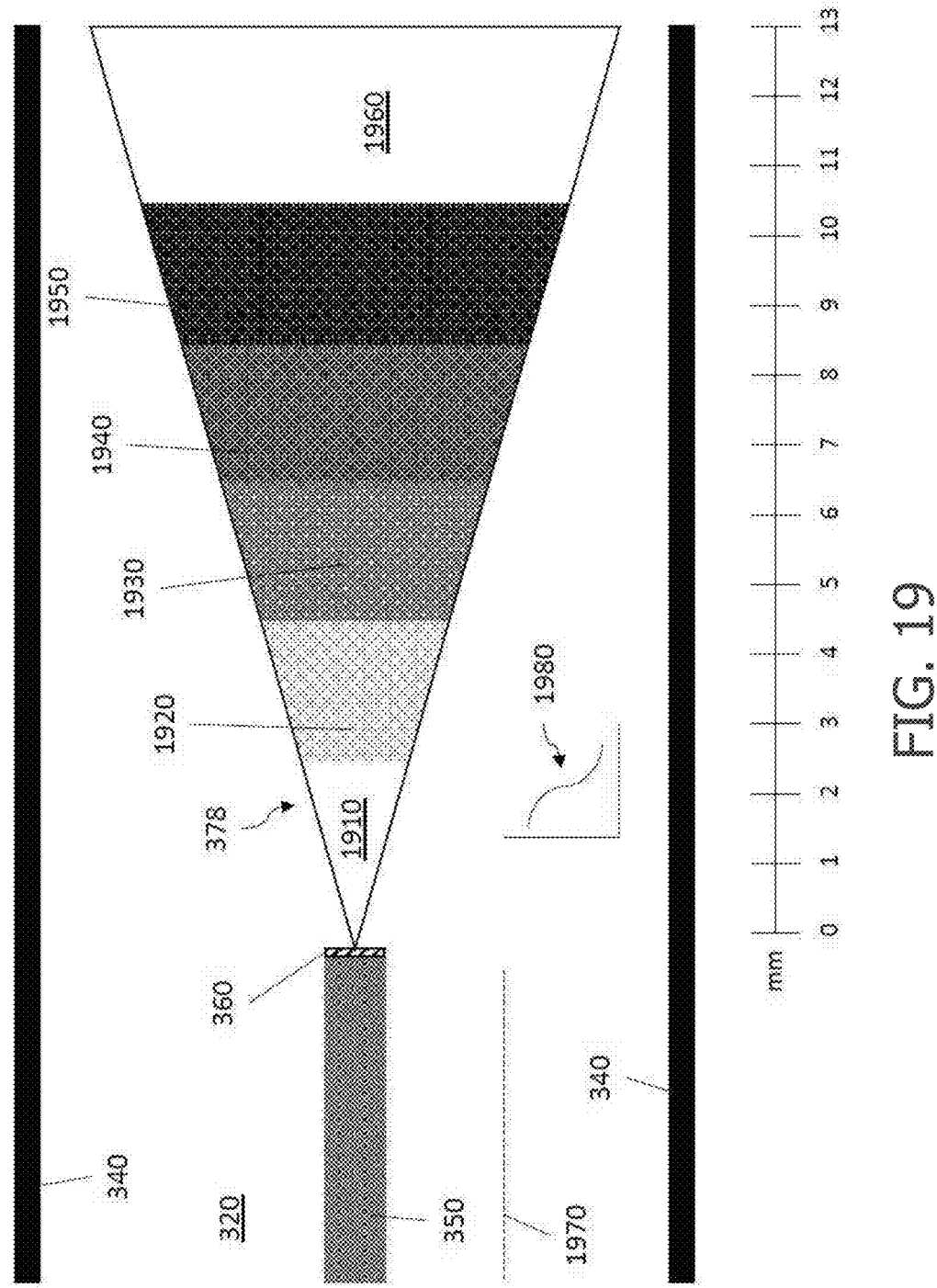
FIG. 19 is a schematic representation of the viewing cone of an ultrasound transducer mounted on the tip of a guidewire within a blood vessel, in accordance with at least one embodiment of the present disclosure.

FIG. 19 is a schematic representation of the viewing cone 378 of an ultrasound transducer 360 mounted on the tip of a guidewire 350 within a blood vessel 320 with vessel walls 340, in accordance with at least one embodiment of the present disclosure. A longitudinal axis 1970 of the guidewire 350 is aligned with the vessel walls 340 and such that a viewing cone 378 of the ultrasound transducer 360 is also aligned with the vessel walls 340 and longitudinal axis 1970. The viewing cone 378 includes a region 1910 that is too close to the transducer 360 for accurate flow measurements, and a region 1960 that is too far from the transducer for accurate flow measurements. In the non-limiting example shown in FIG. 19, the viewing cone also includes a first sample volume 1920 occurring between 2.5-4.5 mm from the transducer 360, a second sample volume 1930 occurring between 4.5-6.4 mm from the transducer 360, a third sample volume 1940 occurring between 6.4-8.4 mm from the transducer 360, and a fourth sample volume 1950 occurring between 8.4-10.4 mm from the transducer 360. The magnitude and quality of flow measurements can be affected by distance from the transducer 360, as shown below.

It should be noted that the velocity profile close to the tip of the guidewire may not be fully developed due to the presence of the wire itself. Therefore, the skew index may be more favorably determined in the sample volumes which are further from the tip of the guidewire (e.g., volumes 1930, 1940, and 1950 may provide better results than volume 1920). Additionally, in some cases, more detailed knowledge about the alignment and placement of the transducer can be developed by determining a skew index at every available sampling depth (e.g., in all four sampling volumes in the example of FIG. 19). The variation in the skew index across the available sampling depths can then be plotted or analyzed. For example, an algorithm may draw, on a display viewable by a clinician, a curve 1980 of skew index vs. measurement depth, or a numerical parameter indicative of the skew index variability, such as a standard deviation or max-min range. Greater variability in the skew index with depth may be indicative of poor transducer alignment, whereas low variability may be indicative of good alignment. In some embodiments, this skew index variability may be assessed by an algorithm (e.g., as part of step 1650 of FIG. 16), such that, for example, alignment is considered to be poor unless both the skew index and the skew index variability fall within identified acceptable ranges.

Figure 20:
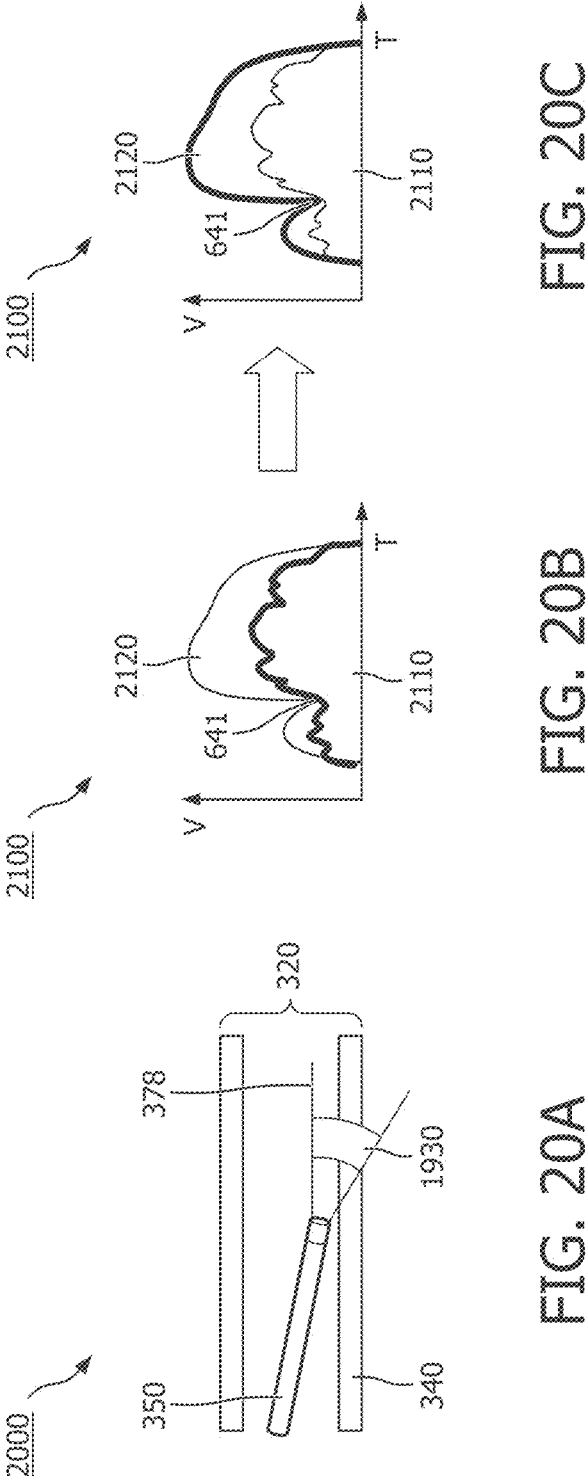
FIG. 20A is a schematic representation of guidewire position and orientation, in accordance with at least one embodiment of the present disclosure.
FIG. 20B is a graph plotting flow velocity vs. time, in accordance with at least one embodiment of the present disclosure.
FIG. 20C is a graph plotting flow velocity vs. time, in accordance with at least one embodiment of the present disclosure.

FIG. 20A is a schematic representation 2000 of guidewire position and orientation, in accordance with at least one embodiment of the present disclosure. In the example shown in FIG. 20, the guidewire 350 is aligned at least partially toward a wall 340 of the blood vessel 320, and is positioned significantly closer to that wall 340 than to the opposite wall. In such cases, the viewing cone 378 may be angled with respect to blood flow within the vessel 320, such that the measured blood velocity is reduced, and is also reduced by the boundary layer effect that causes blood to flow more slowly near the walls of a vessel than near the center. In addition, the viewing cone 378 and sample volume 1930 occur partially within the vessel wall 340.

FIG. 20B is a graph 2100 plotting flow velocity vs. time, in accordance with at least one embodiment of the present disclosure. The graph 2100 includes a set of measurements 2110 that are considered to be valid, a set of measurements 2120 that are considered to be noise, and a dividing line 641 between them that represents the instantaneous peak velocity (IPV) at each time point.

FIG. 20C is a graph 2100 plotting flow velocity vs. time, in accordance with at least one embodiment of the present disclosure. In this example, the skew index or skewness parameter is used to optimize the algorithm to determine the IPV tracing by, for example, adapting the threshold parameters that are used to determine to transition from the signal to the noise. The graph 2100 therefore includes a set of measurements 2110 that are considered to be valid, a set of measurements 2120 that were previously considered to be noise but have been reclassified as valid, and a line 641 that represents the instantaneous peak velocity (IPV) at each time point, now tracing the top of the reclassified measurements 2120.

Figure 21:
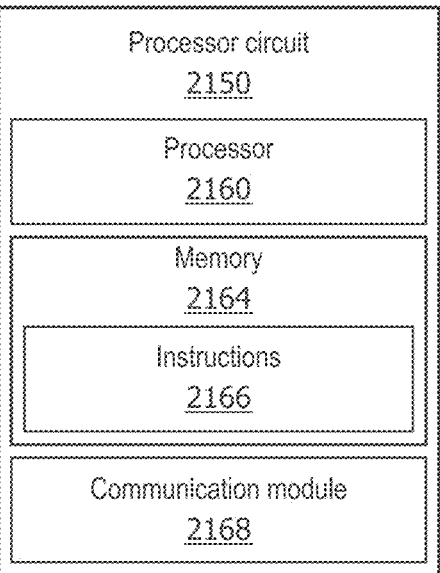
FIG. 21 is a schematic diagram of a processor circuit, in accordance with at least one embodiment of the present disclosure.

FIG. 21 is a schematic diagram of a processor circuit 2150, according to at least one embodiment of the present disclosure. The processor circuit 2150 may be implemented in the intravascular sensing system 100, processing system 306, or other devices or workstations (e.g., third-party workstations, network routers, etc.), or on a cloud processor or other remote processing unit, as necessary to implement the devices, systems, and methods disclosed herein. As shown, the processor circuit 2150 may include a processor 2160, a memory 2164, and a communication module 2168. These elements may be in direct or indirect communication with each other, for example via one or more buses.

The processor 2160 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 2160 may also comprise another hardware device, a firmware device, or any combination thereof configured to perform the operations described herein. The processor 2160 may also be implemented as a combination of computing devices, e.g., a combination of a DSP and a microprocessor, a plurality of microprocessors, one or more microprocessors in conjunction with a DSP core, or any other such configuration.

The memory 2164 may include a cache memory (e.g., a cache memory of the processor 2160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 2164 includes a non-transitory computer-readable medium. The memory 2164 may store instructions 2166. The instructions 2166 may include instructions that, when executed by the processor 2160, cause the processor 2160 to perform the operations described herein. Instructions 2166 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 2168 can include any electronic circuitry and/or logic circuitry to facilitate direct or indirect communication of data between the processor circuit 2150, and other processors or devices. In that regard, the communication module 2168 can be an input/output (I/O) device. In some instances, the communication module 2168 facilitates direct or indirect communication between various elements of the processor circuit 2150 and/or the intravascular measurement system 100. The communication module 2168 may communicate within the processor circuit 2150 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or Fire Wire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

Accordingly, it can be seen that the present disclosure improves the operation of flow-sensing guidewire devices and systems, by permitting the user to understand positioning or alignment problems within a vessel and/or correcting for such problems to construct valid flow measurement data.

The present disclosure may for example be applied for the Philips IGT-D™ business for the existing flow modality, or the Philips FloWire™ or Combo Wire™ that provides simultaneous pressure and flow information. It can also be applied to new flow modalities under the development, both for existing devices and for devices hereinafter developed, either with single transducers or multiple transducers as described above, and comprising either a flow-only sensor or a flow sensor combined with a pressure sensor, or with other sensing modalities. In some embodiments, as part of this development, new patient interface modules (PIMs) may developed that can facilitate the capture of the full raw data signal coming from the flow transducer, to provide raw data for the methods, devices, and systems described herein. The algorithm may include user-viewable features indicative of transducer alignment and/or the quality of flow measurements, or may include automatic changes in the signal strength, waveform, velocity spectrum, or other flow measurement properties without user intervention.

A number of variations are possible on the examples and embodiments described above. For example, the shaped or relative sizes of components may be different than shown herein. The present disclosure may be applied to any flow measurement system incorporating a Doppler flow guidewire. The skew index could also help sonographers orient an external transducer. Other fields of use may include but are not limited to meterology (e.g., Doppler radar), astromony (Doppler effect for electromagnetic waves), fluidic, pneumatic, or hydraulic systems (e.g., flow measurement), or any other field of endeavor where there is a spectrum of wavelengths or velocities, and an assessment of the skewness of the spectrum would be helpful in some way.

The logical operations making up the embodiments of the technology described herein are referred to variously as operations, steps, objects, elements, components, or modules. Furthermore, it should be understood that these may be arranged or performed in any order, unless explicitly claimed otherwise or a specific order is inherently necessitated by the claim language. It should further be understood that the described technology may be employed in single-use and multi-use electrical and electronic devices for medical or nonmedical use.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the reinforced multi-filar conductor bundle. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." The word "comprising" does not exclude other elements or steps, and the indefinite article "a" or "an" does not exclude a plurality. Unless otherwise noted in the claims, stated values shall be interpreted as illustrative only and shall not be taken to be limiting.

The above specification, examples and data provide a complete description of the structure and use of exemplary embodiments of the flow measurement system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An apparatus, comprising:
an intravascular guidewire configured to be positioned within a blood vessel of a patient, wherein the intravascular guidewire comprises a blood flow sensor;
a processor circuit configured for communication with the blood flow sensor, wherein the processor circuit is configured to:
control the blood flow sensor to perform a plurality of velocity measurements of blood flow within the blood vessel;
generate a velocity spectrum based on the plurality of velocity measurements;
calculate an index representative of a shape of the velocity spectrum, wherein the shape represents the plurality of velocity measurements at a particular alignment of the blood pressure sensor in the blood vessel such that the index indicates alignment of the blood flow sensor relative to the blood vessel;
calculate a blood flow parameter using the plurality of velocity measurements when the index satisfies a threshold, wherein the blood flow parameter is different than the index; and
provide the blood flow parameter to a display in communication with the processor circuit.

2. The apparatus of claim 1, wherein the blood flow sensor comprises a forward-facing orientation.

3. The apparatus of claim 1,
wherein the intravascular guidewire comprises a flexible elongate member,
wherein the blood flow sensor is positioned at a distal end of the flexible elongate member.

4. The apparatus of claim 1, wherein the velocity spectrum comprises a histogram of velocity versus frequency of occurrence.

5. The apparatus of claim 1, wherein the index is representative of a skewness of the velocity spectrum.

6. The apparatus of claim 1, wherein the blood flow parameter comprises at least one of: coronary flow reserve (CFR), microvascular resistance index (MR), hyperemic microvascular resistance (HMR), or index of microcirculatory resistance (IMR).

7. The apparatus of claim 1,
wherein the processor circuit is configured to perform a comparison between the index and the threshold to determine when the index satisfies the threshold, and
wherein the the satisfaction of the threshold by the index is representative of a reliability of the plurality of velocity measurements.

8. The apparatus of claim 1, wherein the index comprises a single dimensionless value.

9. The apparatus of claim 1, wherein the index is representative of whether the velocity spectrum is symmetric or asymmetric.

10. The apparatus of claim 9, wherein, when the velocity spectrum is asymmetric, a peak of the velocity spectrum is shifted to the left or shifted to the right.

11. The apparatus of claim 1, wherein the index is calculated by calculating a ratio of a mean velocity to a maximum velocity based on the plurality of velocity measurements.

* * * * *